US012605492B2

(12) United States Patent
Malagoli et al.

(10) Patent No.: US 12,605,492 B2
(45) Date of Patent: Apr. 21, 2026

(54) MANIFOLD ASSEMBLY FOR A PERITONEAL DIALYSIS APPARATUS AND PERITONEAL DIALYSIS APPARATUS COMPRISING SAID MANIFOLD ASSEMBLY

(71) Applicants: BAXTER INTERNATIONAL INC., Deerfield, IL (US); BAXTER HEALTHCARE SA, Glattpark (CH)

(72) Inventors: Marcello Malagoli, Modena (IT); Mauro Suffritti, Modena (IT); Andrea Casali, Modena (IT)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 171 days.

(21) Appl. No.: 18/266,224

(22) PCT Filed: Dec. 9, 2021

(86) PCT No.: PCT/EP2021/085031
§ 371 (c)(1),
(2) Date: Jun. 8, 2023

(87) PCT Pub. No.: WO2022/122941
PCT Pub. Date: Jun. 16, 2022

(65) Prior Publication Data
US 2024/0042112 A1     Feb. 8, 2024

(30) Foreign Application Priority Data
Dec. 10, 2020    (IT) ........................ 102020000030326

(51) Int. Cl.
*A61M 1/28* (2006.01)
*A61M 1/14* (2006.01)

(52) U.S. Cl.
CPC ............ *A61M 1/281* (2014.02); *A61M 1/152* (2022.05); *A61M 1/1524* (2022.05);
(Continued)

(58) Field of Classification Search
CPC ...... A61M 1/15; A61M 1/1524; A61M 1/153; A61M 1/154; A61M 1/155; A61M 1/156;
(Continued)

(56) References Cited

U.S. PATENT DOCUMENTS

2005/0209563 A1     9/2005 Hopping et al.
2015/0367046 A1     12/2015 Ross

FOREIGN PATENT DOCUMENTS

JP        2007-529282        10/2007
WO       2012/129501 A2      9/2012
WO       2019/169081 A2      9/2019

OTHER PUBLICATIONS

Italian Office Action from corresponding Italian Patent Application No. 102020000030326, mailed Jul. 7, 2021, 10 pages (Partial English document).
(Continued)

*Primary Examiner* — John Kim
(74) *Attorney, Agent, or Firm* — K&L Gates LLP

(57) ABSTRACT

A manifold assembly for a peritoneal dialysis apparatus, comprises: a casing delimiting internally a first compartment and a second compartment; a yielding pump tube having a first end connected or connectable to the first compartment and a second end connected or connectable to the second compartment. The yielding pump tube extends outside the casing to be coupled to a peristaltic pump of a cycler of a peritoneal dialysis apparatus. A first pump port and a second pump port are placed on a first side of the casing and ports are placed on a second side of the casing, opposite the first side.

21 Claims, 25 Drawing Sheets

(52) U.S. Cl.
CPC ............ *A61M 1/153* (2022.05); *A61M 1/154*
(2022.05); *A61M 1/155* (2022.05); *A61M
1/156* (2022.05); *A61M 1/1561* (2022.05);
*A61M 1/1563* (2022.05); *A61M 1/282*
(2014.02); *A61M 1/288* (2014.02); *A61M
2205/121* (2013.01); *A61M 2205/123*
(2013.01); *A61M 2205/126* (2013.01); *A61M
2205/128* (2013.01); *A61M 2205/3341*
(2013.01); *A61M 2205/70* (2013.01); *A61M
2205/7536* (2013.01); *A61M 2206/22*
(2013.01)

(58) Field of Classification Search
CPC .. A61M 1/1561; A61M 1/1563; A61M 1/281;
A61M 1/282; A61M 1/288; A61M 1/121;
A61M 1/123; A61M 1/126; A61M 1/128;
A61M 1/3341; A61M 1/70; A61M
1/7536; A61M 2206/22
See application file for complete search history.

(56) References Cited

OTHER PUBLICATIONS

International Search Report from corresponding International Patent Application No. PCT/EP2021/085031, mailed Apr. 12, 2022, 4 pages.
Written Opinion from corresponding International Patent Application No. PCT/EP2021/085031, mailed Apr. 12, 2022, 6 pages.
Japanese Office Action Application No. 2023-534725 dated Oct. 8, 2025—10 pages.

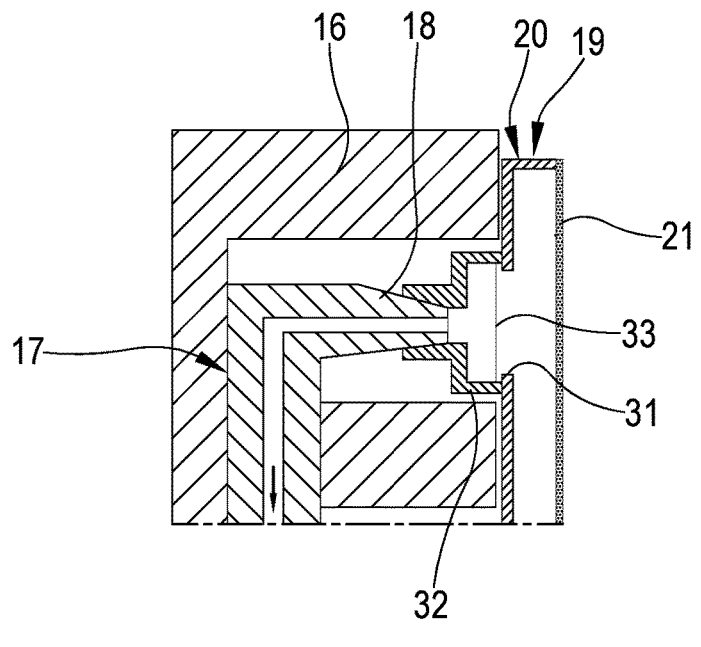
FIG.5
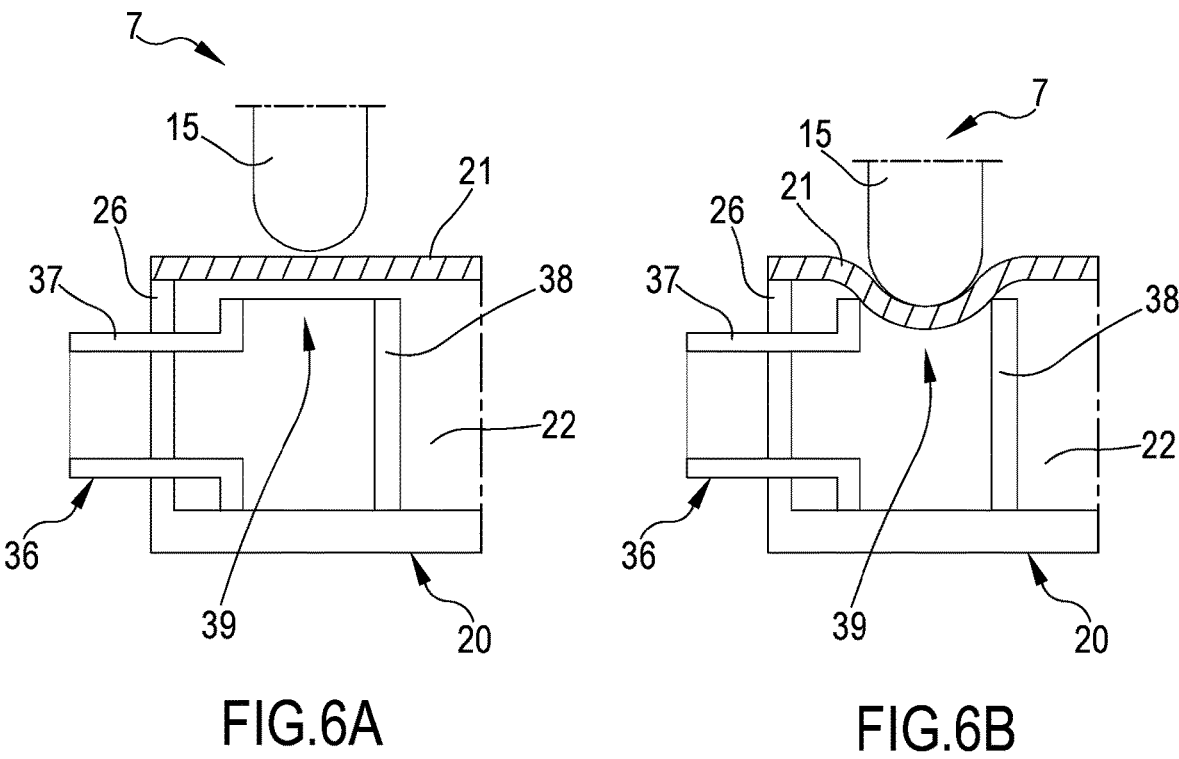
FIG.6A                    FIG.6B

FIG.12

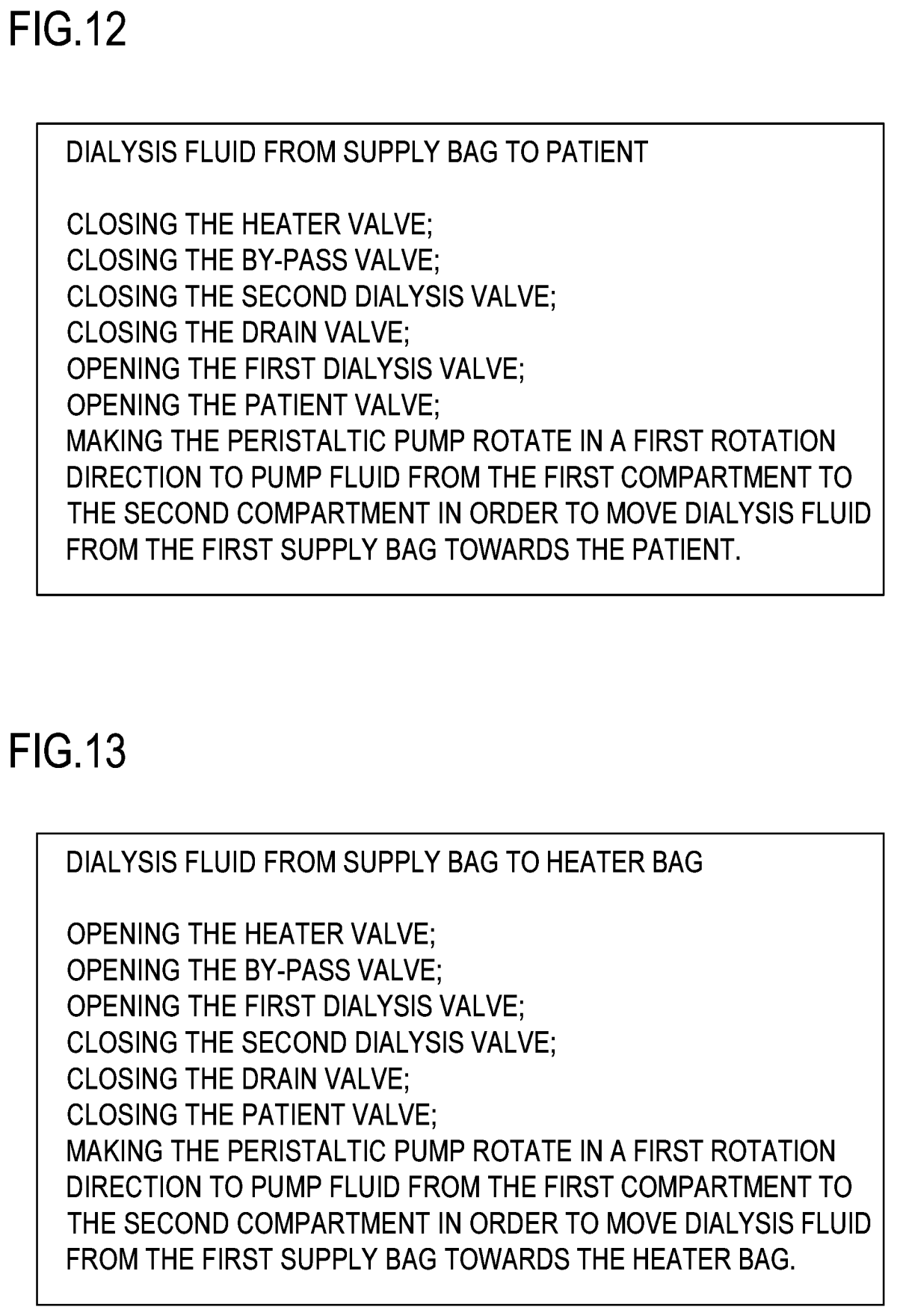

DIALYSIS FLUID FROM SUPPLY BAG TO PATIENT

CLOSING THE HEATER VALVE;
CLOSING THE BY-PASS VALVE;
CLOSING THE SECOND DIALYSIS VALVE;
CLOSING THE DRAIN VALVE;
OPENING THE FIRST DIALYSIS VALVE;
OPENING THE PATIENT VALVE;
MAKING THE PERISTALTIC PUMP ROTATE IN A FIRST ROTATION
DIRECTION TO PUMP FLUID FROM THE FIRST COMPARTMENT TO
THE SECOND COMPARTMENT IN ORDER TO MOVE DIALYSIS FLUID
FROM THE FIRST SUPPLY BAG TOWARDS THE PATIENT.

FIG.13

DIALYSIS FLUID FROM SUPPLY BAG TO HEATER BAG

OPENING THE HEATER VALVE;
OPENING THE BY-PASS VALVE;
OPENING THE FIRST DIALYSIS VALVE;
CLOSING THE SECOND DIALYSIS VALVE;
CLOSING THE DRAIN VALVE;
CLOSING THE PATIENT VALVE;
MAKING THE PERISTALTIC PUMP ROTATE IN A FIRST ROTATION
DIRECTION TO PUMP FLUID FROM THE FIRST COMPARTMENT TO
THE SECOND COMPARTMENT IN ORDER TO MOVE DIALYSIS FLUID
FROM THE FIRST SUPPLY BAG TOWARDS THE HEATER BAG.

FIG.14

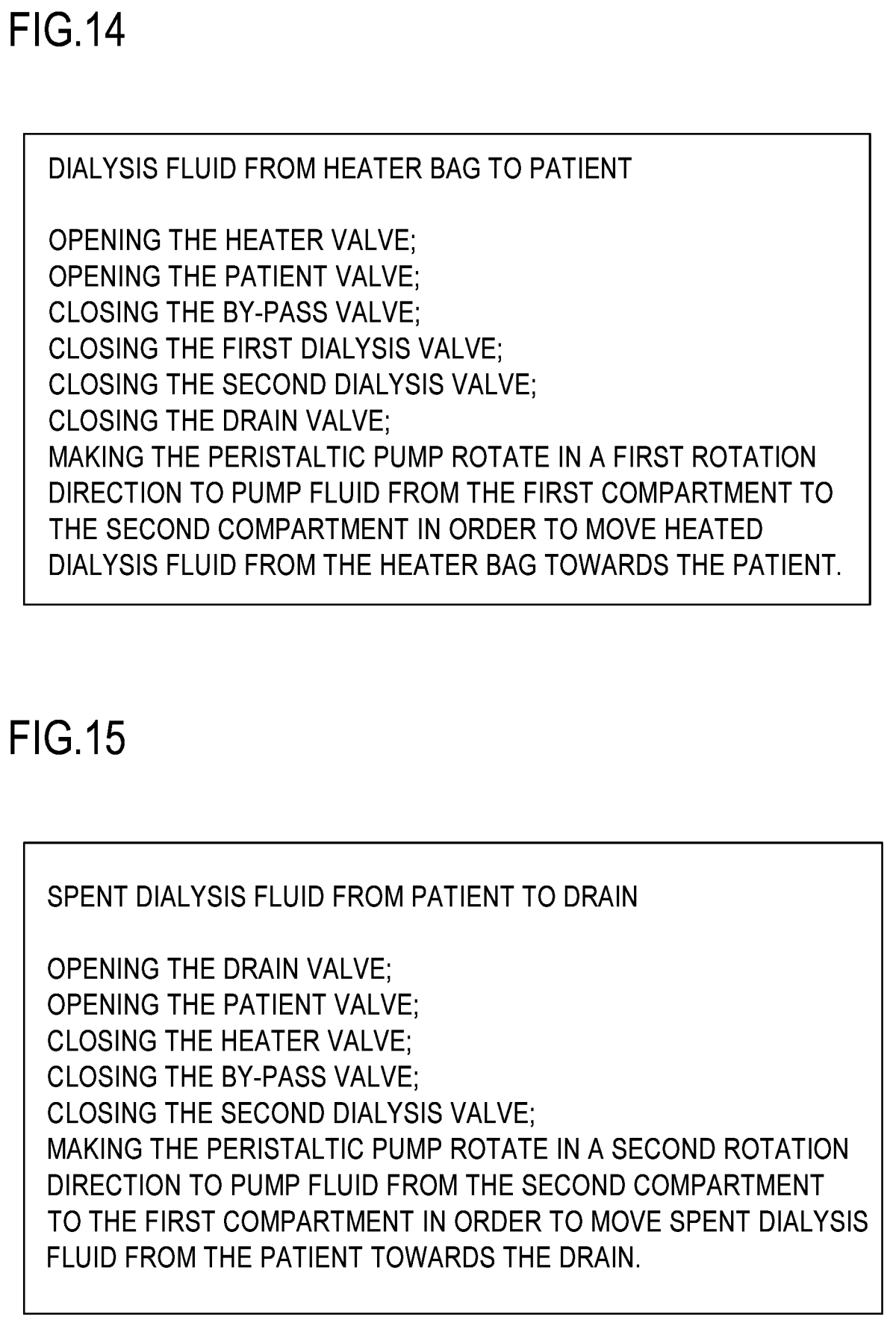

DIALYSIS FLUID FROM HEATER BAG TO PATIENT

OPENING THE HEATER VALVE;
OPENING THE PATIENT VALVE;
CLOSING THE BY-PASS VALVE;
CLOSING THE FIRST DIALYSIS VALVE;
CLOSING THE SECOND DIALYSIS VALVE;
CLOSING THE DRAIN VALVE;
MAKING THE PERISTALTIC PUMP ROTATE IN A FIRST ROTATION
DIRECTION TO PUMP FLUID FROM THE FIRST COMPARTMENT TO
THE SECOND COMPARTMENT IN ORDER TO MOVE HEATED
DIALYSIS FLUID FROM THE HEATER BAG TOWARDS THE PATIENT.

FIG.15

SPENT DIALYSIS FLUID FROM PATIENT TO DRAIN

OPENING THE DRAIN VALVE;
OPENING THE PATIENT VALVE;
CLOSING THE HEATER VALVE;
CLOSING THE BY-PASS VALVE;
CLOSING THE SECOND DIALYSIS VALVE;
MAKING THE PERISTALTIC PUMP ROTATE IN A SECOND ROTATION
DIRECTION TO PUMP FLUID FROM THE SECOND COMPARTMENT
TO THE FIRST COMPARTMENT IN ORDER TO MOVE SPENT DIALYSIS
FLUID FROM THE PATIENT TOWARDS THE DRAIN.

Figure 18:
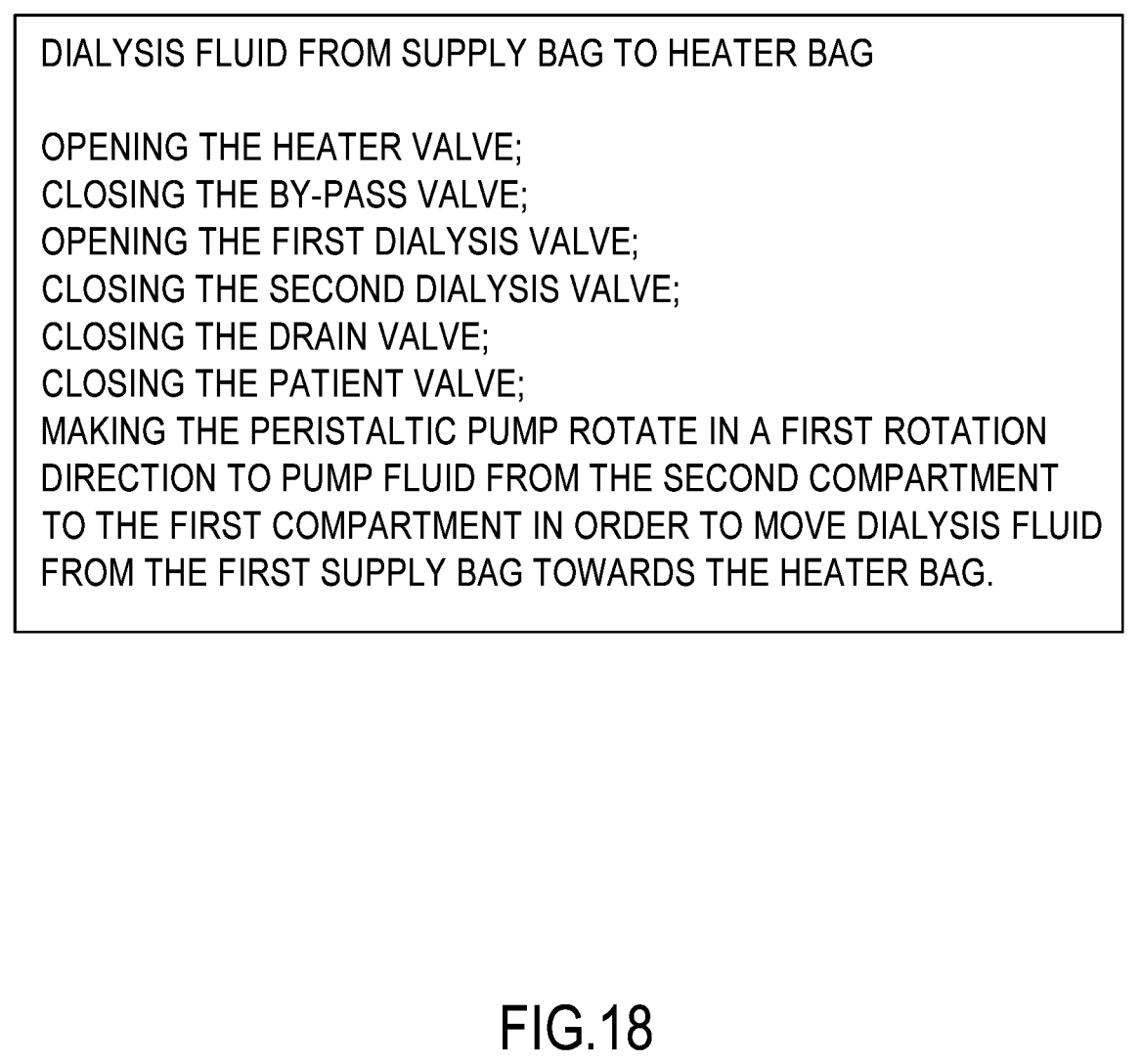

DIALYSIS FLUID FROM SUPPLY BAG TO HEATER BAG

OPENING THE HEATER VALVE;
CLOSING THE BY-PASS VALVE;
OPENING THE FIRST DIALYSIS VALVE;
CLOSING THE SECOND DIALYSIS VALVE;
CLOSING THE DRAIN VALVE;
CLOSING THE PATIENT VALVE;
MAKING THE PERISTALTIC PUMP ROTATE IN A FIRST ROTATION
DIRECTION TO PUMP FLUID FROM THE SECOND COMPARTMENT
TO THE FIRST COMPARTMENT IN ORDER TO MOVE DIALYSIS FLUID
FROM THE FIRST SUPPLY BAG TOWARDS THE HEATER BAG.

MANIFOLD ASSEMBLY FOR A PERITONEAL DIALYSIS APPARATUS AND PERITONEAL DIALYSIS APPARATUS COMPRISING SAID MANIFOLD ASSEMBLY

PRIORITY CLAIM

This application is a national phase entry of PCT/EP2021/085031, filed Dec. 9, 2021, which claims priority to Italian Patent Application No. 102020000030326, filed Dec. 10, 2020, the entire disclosures of which are incorporated herein by reference.

TECHNICAL FIELD

The present disclosure relates to a manifold assembly for a peritoneal dialysis apparatus and to a peritoneal dialysis apparatus comprising said manifold assembly. The present disclosure also relates to a method for controlling the peritoneal dialysis apparatus.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

BACKGROUND

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Known APD systems include a machine or cycler that accepts and actuates a disposable pumping device or cassette having a hard part and a soft part that is deformable for performing pumping and valving operations.

Most of the cycler machines on the market implements pumping systems based on the compression/expansion of the fluids volume within expansion chambers that are part of a disposable device (alternating pumping system). The compression/expansion is performed by the action on the flexible diaphragm incorporated in the chambers of the disposable device, obtaining a continuous flow of boluses of fluid with volumes linked to the volumes of the expansion chambers itself. With such design, the flow rates and thus the fluids volumes exchange are controlled leveraging on the "Ideal Gas Law" combined with the knowledge of the chambers volumes and the pressure monitoring.

Systems of this kind for performing peritoneal dialysis are disclosed, for instance, in US 2011/0092893 and US 2020/0230310.

A main identified disadvantage of such approach refers to the management and modulation of low fluids flow rates, namely flow rate values of an order of magnitude smaller than the volumes of the expansion chambers of the device (typically >15 ml). In such range, the alternating pumping system leads to a discretization of the flow with a decreased level of accuracy. The possibility to manage carefully low flow rates is particularly important in the phase of drainage of fluid from the patient, which often is reported as a painful stage of the treatment for the patient.

Furthermore, the alternating pumping approach results in a slight pulsatile flow that does not represent the best case for the mentioned phase of fluid drainage from the patient and for the administration phase too, in comparison with a smooth and laminar flow regime.

Furthermore, sealing the fluid disposable device with a pneumatic path via a gasket to provide actuation has proven to be a potential field issue, which can delay treatment start time and affect user experience.

Pneumatic cassette systems also produce acoustic noise, which may be a source of customer dissatisfaction.

Some types of cycler machines leverage on the usage of scale for the control of the exchange fluids volumes. Drawback of this approach relate to the need of an accurate and frequent calibration of the scale present on the cycler machine, a procedure exposed to possible errors and which complicates the operations for managing the cycler maintenance.

An additional drawback common to the existing solutions is the lack of a way to manage and remove the potential presence of gas bubbles within the "PD" solutions to be administered to the patient.

Systems of performing peritoneal dialysis through a peristaltic pump are also known. For instance, such systems are disclosed in documents WO2012129501A2, WO2019169081, US2005/0209563, and WO 2018237375.

These systems too have drawbacks related to need for calibration, pulsatile flow, removal of gas bubbles, etc.

It is therefore an object of the present invention to provide a manifold assembly for a peritoneal dialysis apparatus and a peritoneal dialysis apparatus allowing a more accurate and simple control of the fluids flows and an enhanced monitoring of the effectiveness of the peritoneal dialysis treatment.

It is an object of the present invention to provide a manifold assembly for a peritoneal dialysis apparatus and a peritoneal dialysis apparatus capable to guarantee a continuous flow with the possibility to modulate and assure high accuracy, also at a low flow rate range (e.g. 5-10 ml/min).

It is a further object of the present invention to provide a manifold assembly and an apparatus able to manage the fluid levels and to assure to keep the fluid level within a defined range.

It is a further object of the present invention to provide a manifold assembly and an apparatus that attenuates the effect of the peristalsis of the pump, providing a flow that does not present the pulsation typical of alternating pumping systems or of the prior art systems employing peristaltic pumps.

It is a further object of the present invention to provide a manifold assembly and an apparatus providing a possible reduction of treatment times.

It is a further object of the present invention to provide a manifold assembly and an apparatus allowing the detection of the potential occurrence of extreme negative pressure values in the chamber compartment connected to the drain and bags lines.

It is a further object of the present invention to provide a manifold assembly and an apparatus capable of removing gas bubbles potentially present in the "PD" solutions before administration to the patient.

It is a further object of the present invention to provide a manifold assembly and an apparatus offering the possibility to monitor the pressure values within a chamber compartment of said manifold assembly connected to the patient line and to adjust the fluid level of the chamber compartment.

It is a further object of the present invention to provide a manifold assembly which is reliable and can be easily interfaced/coupled to the hardware components of a cycler of the apparatus.

It is a further object of the present invention to provide a manifold assembly which can be easily handled and easily mounted/removed on/from the cycler of the apparatus by a user.

SUMMARY

At least one of the above objects is substantially reached by a manifold assembly for a peritoneal dialysis apparatus and a peritoneal dialysis apparatus according to one or more of the appended claims.

A manifold assembly for a peritoneal dialysis apparatus, a peritoneal dialysis apparatus and a method for controlling the peritoneal dialysis apparatus according to aspects of the invention and capable of achieving one or more of the above objects are here below disclosed.

A $1^{st}$ aspect concerns a manifold assembly for a peritoneal dialysis apparatus, comprising: a casing delimiting internally a first compartment and a second compartment; a yielding pump tube having a first end connected or connectable to the first compartment and a second end connected or connectable to the second compartment, wherein the yielding pump tube extends outside the casing to be coupled to a peristaltic pump of a cycler of a peritoneal dialysis apparatus; a plurality of line tubes each having a first end connected or connectable to the first compartment or to the second compartment and a second end connected or connectable to a fluid source or to a drain or to a patient.

Optionally, the plurality of line tubes comprises: a patient line tube having a first end connected or connectable to the second compartment and a second end connectable to a peritoneal cavity of a patient; at least one fluid line tube having a first end connected or connectable to the first compartment and a second end connected or connectable to a fluid source and/or to a drain; optionally, at least one fluid line tube having a first end connected or connectable to the second compartment and a second end connected or connectable to a fluid source.

The first compartment, the yielding pump tube and the second compartment delimit together a fluid path extending between said at least one fluid line tube, having the first end connected to the first compartment, and the patient line tube, to allow fluid flow at least from said at least one fluid line tube, having the first end connected to the first compartment, to the patient line tube or from the patient line tube to said at least one fluid line tube, having the first end connected to the first compartment, when the peristaltic pump of the cycler is actuated.

A $2^{nd}$ aspect concerns a peritoneal dialysis apparatus comprising the manifold assembly of the $1^{st}$ aspect or of one or more of the following aspects.

A $3^{rd}$ aspect concerns a method for controlling the peritoneal dialysis apparatus of the previous aspect.

In a $4^{th}$ aspect according to the $1^{st}$ aspect, the manifold assembly comprises hooking elements configured to hook, in removable manner, said disposable assembly to the cycler, optionally to a front panel of the cycler; and/or the casing is shaped to be hooked in removable manner to the cycler, optionally to a front panel of the cycler; optionally the manifold assembly is, at least in part, disposable or reusable.

In a $5^{th}$ aspect, which may be used with any other aspect described herein, the second compartment delimits at least one expansion chamber configured to attenuate pressure pulsations from the peristaltic pump; optionally the at least one expansion chamber is at least in part delimited by one soft membrane; optionally, wherein said at least one soft membrane is made of a plastic sheet, optionally polyvinyl chloride sheet.

In a $6^{th}$ aspect, which may be used with any other aspect described herein, the casing has a substantially flattened shape.

In a $6^{th}$ bis aspect, which may be used with any other aspect described herein, the casing is provided with a front, a back and a plurality of sides; optionally the back is configured to be coupled to a front panel of the cycler.

In a $6^{th}$ ter aspect according to the previous aspect, the first pump port and the second pump port are placed on a first side of the casing while the ports are placed on a second side of the casing, opposite the first side.

In a $6^{th}$ quarter aspect according to the previous aspect, the casing has a substantially rectangular outline with two long sides and two short sides; optionally, the first side and the second side are both long sides of the casing.

In a $7^{th}$ aspect, which may be used with any other aspect described herein, the first compartment and/or the second compartment have, at least in part, a flattened shape.

In a $8^{th}$ aspect, which may be used with any other aspect described herein, said at least one fluid line tube comprises: at least one dialysis fluid line tube; optionally the at least one dialysis fluid line tube has the first end connected to the first compartment or the at least one dialysis fluid line tube has the first end connected to the second compartment.

In a $9^{th}$ aspect according to aspect 8, the fluid source connected to the second end of said least one dialysis fluid line tube is a supply bag.

In a $10^{th}$ aspect according to aspect 8 or 9, said at least one fluid line tube comprises: a plurality of dialysis fluid line tubes, optionally a first dialysis fluid line tube and a second dialysis fluid line tube.

In a $11^{th}$ aspect according to aspect 10, each dialysis fluid line tube is connected to a respective supply bag.

In a $12^{th}$ aspect, which may be used with any other aspect described herein, said at least one fluid line tube comprises: a heater line tube; optionally, the heater line tube has the first end connected to the first compartment.

In a $13^{th}$ aspect according to aspect 12, the fluid source connected to the second end of the heater line tube is a heater bag.

In a $14^{th}$ aspect according to aspect 13, the heater bag is configured to be coupled to a heater of the cycler.

In a $14^{th}$ bis aspect according to aspect 11, an auxiliary in-line heater is placed on said at least one fluid line tube to heat the dialysis fluid while flowing through said dialysis fluid line tube.

In a $15^{th}$ aspect, which may be used with any other aspect described herein, said at least one fluid line tube comprises: a drain fluid line tube; optionally, the drain fluid line tube has the first end connected to the first compartment; optionally, said at least one fluid line tube comprises also an auxiliary drain fluid line tube having a first end connected to the second compartment.

In a $16^{th}$ aspect according to aspect 15, the drain fluid line tube, and optionally auxiliary drain fluid line tube, has/have the second end connected or connectable to the drain: optionally, the drain fluid line tube merges with the auxiliary drain fluid line tube in a common drain line before reaching the drain.

In a $17^{th}$ aspect, which may be used with any other aspect described herein, the yielding pump tube has a curved shape.

In a $18^{th}$ aspect, which may be used with any other aspect described herein, the yielding pump tube is shaped as a loop or as an eyelet, optionally, having an omega "$\Omega$" shape.

In a $19^{th}$ aspect, which may be used with any other aspect described herein, the casing comprises a first pump port connected or connectable to the first end of the yielding pump tube and in fluid communication with the first compartment.

In a $20^{th}$ aspect according to aspect 19, the casing comprises a second pump port connected or connectable to the second end of the yielding pump tube and in fluid communication with the second compartment.

In a $21^{st}$ aspect according to aspect 19 and 20, the first pump port and the second pump port diverge from each other away from the casing.

In a $22^{nd}$ aspect, which may be used with any other aspect described herein, the casing comprises a plurality of ports each connected or connectable to the first end of one line tube.

In a $22^{nd}$ bis aspect according to the previous aspect 22 and to aspect 6 ter, the first pump port, the second pump port and the plurality of ports protrudes from the respective side of the casing; optionally, each of the first pump port, the second pump port and the plurality of ports is shaped like an hollow cylinder; optionally, the hollow cylinders of the plurality of ports are parallel to each other.

In a $22^{nd}$ ter aspect, which may be used with any other aspect described herein, the casing comprises a patient port connected or connectable to the first end of the patient line tube and in fluid communication with the second compartment.

In a $23^{rd}$ aspect according to aspect 22 ter, the patient port comprises a respective valve or part of a valve, i.e. a patient valve; or, alternatively, a clamp of the cycler may be coupled to the patient line tube to pinch said tube.

In a $24^{th}$ aspect according to aspect 22 ter or 23, said at least one patient port has a seat for accommodating, at least partially, a respective occlusion element of the cycler.

In a $25^{th}$ aspect according to aspect 24 when used with aspect 23, the occlusion element of the cycler is part of the patient valve.

In a $26^{th}$ aspect according to aspect 23 or to aspect 24 or 25 when used with aspect 23, when the valve of the patient port is open, the patient line tube is in fluid communication with the second compartment; when the valve of the patient port is closed, fluid communication between the patient line tube and the second compartment is prevented.

In a $27^{th}$ aspect, which may be used with any other aspect described herein, the casing comprises at least one fluid port connected or connectable to the first end of said at least one fluid line tube and in fluid communication with the first compartment or with the second compartment.

In a $28^{th}$ aspect according to aspect 27, said at least one fluid port comprises a respective valve or part of a valve, i.e. a fluid valve; or, alternatively, a clamp of the cycler may be coupled to the fluid line tube to pinch said tube.

In a $29^{th}$ aspect according to aspect 27 or 28, said at least one fluid port has a seat for accommodating, at least partially, a respective occlusion element of the cycler.

In a $30^{th}$ aspect according to aspect 29 when used with aspect 28, the occlusion element of the cycler is part of the fluid valve.

In a $31^{st}$ aspect according to aspect 28 or to aspect 29 or 30 when used with aspect 28, when the valve of said at least one fluid port is open, said at least one fluid line tube is in fluid communication with the first compartment or with the second compartment; when the valve of said at least one fluid port is closed, fluid communication between said at least one fluid line tube and the first compartment or second compartment is prevented.

In a $32^{nd}$ aspect according to any of aspects 27 to 31 when used with any of aspects 8 to 11, the at least one fluid port comprises at least one dialysis fluid port connected to the first end of said at least one dialysis fluid line tube; optionally the at least one fluid port comprises a first dialysis fluid port connected to the first end of a first dialysis fluid line tube and a second dialysis fluid port connected to the first end of a second dialysis fluid line tube.

In a $33^{rd}$ aspect according to aspect 32, a second end of the first dialysis fluid line tube is connected to a first supply bag and a second end of the second dialysis fluid line tube is connected to a second supply bag.

In a 34th aspect according to aspect 32 or 33, said at least one dialysis fluid port comprises a respective valve or part of a valve, i.e. a dialysis valve, optionally a first dialysis valve and a second dialysis valve.

In a 35th aspect according to any of aspects 32 to 34, said at least one dialysis fluid port has a seat for accommodating, at least partially, a respective occlusion element of the cycler.

In a 36th aspect according to aspect 35 when used with aspect 34, the occlusion element of the cycler is part of the dialysis valve.

In a 37th aspect according to aspect 34, or to aspect 35 or 36 when used with aspect 34, when the valve of said at least one dialysis fluid port is open, said at least one dialysis fluid line tube is in fluid communication with the first compartment or with the second compartment; when the valve of said at least one dialysis fluid port is closed, fluid communication between said at least one dialysis fluid line tube and the first compartment or second compartment is prevented.

In a 38th aspect according to any of aspects 27 to 31 when used with any of aspects 12 to 14, said at least one fluid port comprises a heater port connected to the first end of the heater line tube.

In a 39th aspect according to aspect 38, said heater port comprises a respective valve or part of a valve, i.e. heater valve.

In a 40th aspect according to aspect 38 or 39, said heater port has a seat for accommodating, at least partially, a respective occlusion element of the cycler.

In a 41st aspect according to aspect 40 when used with aspect 39, the occlusion element of the cycler is part of the heater valve.

In a 42nd aspect according to aspect 39 or to aspect 40 or 41 when used with aspect 39, when the valve of the heater port is open, the heater line tube is in fluid communication with the first compartment; when the valve of the heater port is closed, fluid communication between the heater line tube and the first compartment is prevented.

In a 43rd aspect according to any of aspects 27 to 31 when used with aspect 15 or 16, said at least one fluid port comprises a drain port connected to the first end of the drain fluid line tube; optionally, said at least one fluid port comprises an auxiliary drain port connected to the first end of the auxiliary drain fluid line tube.

In a 44th aspect according to aspect 43, said drain port comprises a respective valve or part of a valve, i.e. drain valve.

In a 45th aspect according to aspect 43 or 44, said drain port has a seat for accommodating, at least partially, a respective occlusion element of the cycler.

In a 46th aspect according to aspect 45 when used with aspect 44, the occlusion element of the cycler is part of the drain valve.

In a 47th aspect according to aspect 44 or to aspect 45 or 46 when used with aspect 44, when the valve of the drain port is open, the drain line tube is in fluid communication with the first compartment; when the valve of the drain port is closed, fluid communication between the drain line tube and the first compartment is prevented.

In a 48th aspect according to aspect 12, the casing comprises a by-pass channel in fluid communication with the first compartment, with the second compartment and with the heater line tube.

In a 48th bis aspect to aspect 48, the by-pass channel is at least in part delimited by a cover joined to an exterior surface of the casing, optionally to the front of the casing.

In a 49th aspect according to aspect 48, the second compartment comprises a by-pass port in fluid communication with the by-pass channel.

In a 50th aspect according to aspect 49, the by-pass port comprises a respective valve or part of a valve, i.e. by-pass valve.

In a 51st aspect according to aspect 49 or 50, the by-pass port has a seat for accommodating, at least partially, a respective occlusion element of the cycler.

In a 52nd aspect according to aspect 51, the occlusion element of the cycler is part of the by-pass valve.

In a 53rd aspect according to aspect 50 or to aspect 51 or 52 when used with aspect 50, when the valve of the by-pass port is open, the heater line tube is in fluid communication with the second compartment; when the valve of the by-pass port is closed, fluid communication between the heater line tube and the second compartment is prevented.

In a 54th aspect, which may be used with any other aspect described herein, the first compartment is a first elongated passage.

In a 55th aspect according aspect 54, the first compartment extends between one of the at least one fluid line tube and the first end of the yielding pump tube.

In a 56th aspect according to aspect 54 or 55, the first elongated passage is substantially U-shaped.

In a 57th aspect according to any of aspects 54 to 56, the first end of said at least one fluid line tube and the first end of the drain fluid line tube are arranged one after the other along the first elongated passage.

In a 58th aspect, which may be used with any other aspect described herein, when the assembly is properly mounted on the cycler, the first end of said at least one fluid line tube and the first end of the drain fluid line tube are arranged one above the other.

In a 59th aspect according to any of aspects 54 to 56 when used with aspects 10 to 16, the first end of the heater line tube and the first end of the drain fluid line tube and optionally also the first ends of the plurality of dialysis fluid line tubes, are arranged one after the other along the first elongated passage; optionally along a longest stretch of the U-shaped first elongated passage.

In a 60th aspect according to aspects 10 to 16, when the assembly is properly mounted on the cycler, the drain line tube is arranged above the patient line tube and, optionally, below the heater bag tube and the plurality of dialysis fluid line tubes; or, alternatively, when the assembly is properly mounted on the cycler, the drain line tube is arranged above the patient line tube, the heater bag tube and the plurality of dialysis fluid line tubes; optionally, when the manifold assembly is properly mounted on the cycler, the drain line tube is arranged close to a top of the casing; optionally, when the manifold assembly is properly mounted on the cycler, the patient line tube is arranged close to a bottom of the casing.

In a 61st aspect according to aspect 56 or to aspect 57 when used with aspect 56, the first end of the yielding pump tube is connected to an extremity of the U-shaped elongated passage.

In a 62rd aspect according to aspect 56 or to aspect 57 when used with aspect 56, the second compartment is partly surrounded by the U-shaped elongated passage.

In a 63rd aspect according to aspect 5, a plurality of expansion chambers are delimited in the second compartment.

In a 64th aspect according to aspect 63, at least two, optionally three expansion chambers are delimited in the second compartment.

In a $65^{th}$ aspect, which may be used with any other aspect described herein, an inner volume of the second compartment, comprising the at least one expansion chamber, is greater than an inner volume of the first compartment.

In a $66^{th}$ aspect, which may be used with any other aspect described herein, an inner volume of the second compartment is between 50 cm³ and 60 cm³, optionally between 54 cm³ and 57 cm³.

In a $67^{th}$ aspect, which may be used with any other aspect described herein, an inner volume of the first compartment is between 8 cm³ and 20 cm³, optionally between 14 cm³ and 18 cm³.

In a $68^{th}$ aspect according to aspect 63 or 64 when used with any of aspects 54 to 57, the second compartment comprises a septum delimiting a second elongated passage in fluid communication with said at least one expansion chamber.

In a $69^{th}$ aspect according to aspect 68, the second elongated passage has a first extremity connected to the second end of the yielding pump tube and a second extremity communicating with said at least one expansion chamber.

In a $70^{th}$ aspect according to aspect 68 or 69, the second compartment comprises a main central part divided from the second elongated passage by the septum.

In a $71^{st}$ aspect according to aspect 70, the at least one expansion chamber is delimited in the main central part.

In a $72^{nd}$ aspect according to aspect 5, the casing comprises at least one recess/protrusion delimiting said at least one expansion chamber, such that said at least one expansion chamber has a depth greater than a depth of a remaining part of the second compartment; optionally the recess/protrusion protrude from a front of the casing.

In a $73^{rd}$ aspect according to aspect 72, an external shape of the recess/protrusion is configured to be grabbed by one hand of a user.

In a $74^{th}$ aspect, which may be used with any other aspect described herein, the casing has an external flat surface for interfacing with at least one level sensor of the cycler, optionally with two level sensors of the cycler.

In a $75^{th}$ aspect according to aspect 74, said at least one level sensor is a capacitive sensor.

In a $76^{th}$ aspect according to aspect 74 or 75, said at least one level sensor is configured to be placed outside the casing.

In a $77^{th}$ aspect according to any of aspects 74 to 76, when the assembly is properly mounted on the cycler, the two level sensors are one above the other.

In a $78^{th}$ aspect, which may be used with any other aspect described herein, the casing has through apertures passing through; optionally said through apertures are configured to engage with retaining elements of the cycler, optionally positioned on a front panel of the cycler.

In a $79^{th}$ aspect according to aspect 78, a plurality of expansion chambers and/or recesses/protrusions are delimited in the second compartment and the apertures are positioned between two of said plurality of expansion chambers and/or recesses/protrusions.

In a $80^{th}$ aspect, which may be used with any other aspect described herein, when the assembly is properly mounted on the cycler, an upper part of the second compartment delimits an air buffer volume; optionally, the air buffer volume is in communication with a pressure transducer and/or an air pump of the cycler.

In a $81^{st}$ aspect according to aspect 80, the casing comprises a breathable membrane configured to put into communication the pressure transducer and/or the air pump of the cycler with the upper part of the second compartment and/or with the air buffer volume, when the manifold assembly is properly mounted on the cycler.

In a $82^{rd}$ aspect according to aspect 81, the breathable membrane is welded or glued to a rigid shell of the casing.

In a $83^{rd}$ aspect according to aspect 82, the breathable membrane is joined to an edge of hole in the rigid shell.

In a $84^{th}$ aspect according to aspect 82, a rigid frame supports the breathable membrane; optionally the breathable membrane is joined to a rigid frame and the rigid frame is joined to an edge of a hole in the rigid shell; optionally, the hole in the casing is fashioned in the front of the casing.

In a $85^{th}$ aspect according to any of aspects 81 to 84, the breathable membrane is hydrophobic.

In a $86^{th}$ aspect, which may be used with any other aspect described herein, the casing comprises a rigid shell and at least one soft membrane.

In a $87^{th}$ aspect according to aspect 86, the rigid shell is made of rigid plastic, optionally molded.

In a $88^{th}$ aspect according to aspect 86 or 87, said at least one soft membrane is made of a plastic sheet, optionally Polyvinyl chloride sheet.

In a $89^{th}$ aspect according to any of aspects 86 to 88, said at least one soft membrane is welded or glued to the rigid shell.

In a $90^{th}$ aspect according to any of aspects 86 to 89, the rigid shell delimits a front and sides of the casing and said at least one soft membrane is a back of the casing; optionally, an area of said at least one soft membrane is configured to be coupled to displacement sensor of the cycler when the assembly is properly mounted on the cycler; optionally, said area faces a zone of the first compartment; optionally, said area is at an elbow the substantially U-shaped first elongated passage.

In a $91^{st}$ aspect according to any of aspects 86 to 89 when used with aspects 24 and 29, said at least one soft membrane faces the seat of said at least one fluid port and of the patient port; wherein the soft membrane is configured to be deformed by the occlusion element of the of the cycler, when said occlusion element is accommodated, at least in part, in the seat, to close the patient port and/or the fluid port.

In a $92^{rd}$ aspect according to any of aspects 86 to 89 when used with aspect 51, said at least one soft membrane faces the seat of the by-pass port; wherein the soft membrane is configured to be deformed by the occlusion element, when said occlusion element is accommodated, at least in part, in the seat, to close the by-pass port.

In a $93^{rd}$ aspect, which may be used with any other aspect described herein, the peritoneal dialysis apparatus comprises a cycler.

In a $94^{th}$ aspect according to aspect 93, the cycler comprises a peristaltic pump, optionally a roller peristaltic pump; optionally the peristaltic pump comprises one or more pressing elements, optionally one or more pressing rollers; optionally the peristaltic pump comprises two pressing elements angularly spaced of 180°.

In a $95^{th}$ aspect according to aspect 94, the yielding pump tube is placed in part or is configured to be placed in part around a rotor of the peristaltic pump.

In a $96^{th}$ aspect according to any of aspects 93 to 95, the cycler comprises at least one level sensor, optionally two level sensors; optionally, the cycler comprises at least one displacement sensor.

In a $97^{th}$ aspect according to any of aspects 93 to 96 when used with aspect 13 or 14, the cycler comprises a heater, wherein the heater bag is configured to be coupled to the heater.

In a 98<sup>th</sup> aspect according to any of aspects 93 to 97 when used with aspects 22 and 27, the cycler comprises a plurality of occlusion elements; wherein each occlusion element is configured to be accommodated at least in part in a respective seat of the fluid ports and of the patient port; or, alternatively, wherein the fluid ports and the patient port do not have any seat and each occlusion element is a clamp configured to pinch one of the fluid line tubes or the patient tube.

In a 99<sup>th</sup> aspect according to aspect 98 when used with any of aspects 86 to 92, each occlusion element together with a part of the soft membrane and a respective seat defines a valve or each clamp together with a part of the fluid line tube defines a pinch valve; optionally, a heater valve of the heater port, a by-pass valve of the by-pass port, a first dialysis valve of the first dialysis port, a second dialysis valve of the second dialysis port, a drain valve of the drain port, a patient valve of the patient port; optionally, an auxiliary drain valve of the auxiliary drain port.

In a 100<sup>th</sup> aspect according to any of aspects 93 to 97 when used with any of aspects 81 to 85, the cycler comprises a pressure transducer and/or an air pump configured to be put into communication with the breathable membrane of the casing and/or with the air buffer volume.

In a 101<sup>st</sup> aspect according to aspect 100, the cycler comprises an air conduit in air communication with the pressure transducer and/or the air pump, wherein the air conduit has a coupling end configured to be coupled to the breathable membrane of the casing.

In a 102<sup>rd</sup> aspect according to aspect 94 or 95 or to any of aspects 96 to 101 when used with aspect 94 or 95, the cycler comprises a box having a front panel, wherein a rotor of the peristaltic pump is positioned on the front panel.

In a 103<sup>rd</sup> aspect according to aspect 102, the cycler comprises a lid movable between a closed position, in which the lid covers the front panel, and an open position, in which the lid is spaced from the front panel to allow access to said front panel.

In a 104<sup>th</sup> aspect according to aspect 103, the front panel and/or the lid is/are so shaped to receive at least part of the manifold assembly; optionally the front panel is so shaped to receive and hold the manifold assembly; optionally the front panel comprises retaining elements configured to be coupled to the manifold assembly and hold the manifold assembly, optionally in removable manner.

In a 105<sup>th</sup> aspect according to aspect 103 or 104, when the manifold assembly is properly mounted on the cycler, said manifold assembly is closed between the front panel and the lid.

In a 106<sup>th</sup> aspect according to any of aspects 103 to 105 when used with aspect 101, at least the coupling end of the air conduit is mounted on the lid or on the front panel and, when the manifold assembly is properly mounted on the cycler, said coupling end is coupled to the breathable membrane of the casing.

In a 107<sup>th</sup> aspect according to any of aspects 103 to 106 when used with aspect 96, said at least one level sensor is mounted on the front panel or on the lid.

In a 108<sup>th</sup> aspect according to any of aspects 103 to 106 when used with aspect 24 and 29, said occlusion elements are mounted on the front panel or on the lid.

In a 109<sup>th</sup> aspect according to one or more of aspects 93 to 108, the cycler comprises a control unit, a motor of the peristaltic pump, actuators of the occlusion elements; wherein the control unit is operationally connected to said motor, to said actuators, to the pressure transducer and/or the air pump, to the at least one level sensor, optionally to the displacement sensor; wherein the control unit is configured/programmed to control operation of the peritoneal dialysis apparatus.

In a 110<sup>th</sup> aspect according to aspect 3 or to aspect 109 when used with aspect 99, the method comprises or the control unit in configured to perform the following steps: opening the first dialysis valve and the patient valve; closing the heater valve, the by-pass valve, the second dialysis valve and the drain valve; making the peristaltic pump rotate in a first rotation direction to pump fluid from the first compartment to the second compartment in order to move dialysis fluid from the first supply bag towards the patient.

In a 111<sup>st</sup> aspect according to aspect 3 or to aspect 109 when used with aspect 99, the method comprises or the control unit in configured to perform the following steps: opening, the first dialysis valve, the by-pass valve; closing, the heater valve, the second dialysis valve, the drain valve and the patient valve; making the peristaltic pump rotate in a first rotation direction to pump fluid from the first compartment to the second compartment in order to move dialysis fluid from the first supply bag towards the heater bag.

In a 112<sup>rd</sup> aspect according to aspect 3 or to aspect 109 when used with aspect 99, the method comprises or the control unit in configured to perform the following steps: opening the heater valve and the first dialysis valve; closing the by-pass valve, the second dialysis valve, the drain valve and the patient valve; making the peristaltic pump rotate in a second rotation direction to pump fluid from the second compartment to the first compartment in order to move dialysis fluid from the first supply bag towards the heater bag.

In a 113<sup>rd</sup> aspect according to aspect 3 or to aspect 109 when used with aspect 99, the method comprises or the control unit in configured to perform the following steps: opening the heater valve and the patient valve; closing the by-pass valve, the first dialysis valve, the second dialysis valve and the drain valve; making the peristaltic pump rotate in a first rotation direction to pump fluid from the first compartment to the second compartment in order to move heated dialysis fluid from the heater bag towards the patient.

In a 114<sup>th</sup> aspect according to aspect 3 or to aspect 109 when used with aspect 99, the method comprises or the control unit in configured to perform the following steps: opening the drain valve and the patient valve; closing the heater valve, the by-pass valve, the first dialysis valve, the second dialysis valve; making the peristaltic pump rotate in a second rotation direction to pump fluid from the second compartment to the first compartment in order to move spent dialysis fluid from the patient towards the drain.

In a 115<sup>th</sup> aspect according to aspect 3 or to aspect 109 when used with aspect 99, the method comprises or the control unit in configured to perform the following steps: opening the by-pass valve and the drain valve; closing the heater valve, the patient valve, the first dialysis valve, the second dialysis valve; making the peristaltic pump rotate in a second rotation direction to pump priming fluid from the second compartment to the first compartment and from the heater bag to the drain and performing a priming step.

In a 116<sup>th</sup> aspect according to aspect 3 or to aspect 109 when used with aspect 99, the method comprises or the control unit in configured to perform the following steps: opening the heater valve and the auxiliary drain valve; closing the, the patient valve, the first dialysis valve, the second dialysis valve, the drain valve; making the peristaltic pump rotate in a first rotation direction to pump priming fluid from the first compartment to the second compartment and from the heater bag to the drain and performing a priming step.

In a 117$^{th}$ aspect according to aspect 3 or to aspect 109 when used with aspect 99, the method comprises or the control unit in configured to perform the following steps: opening the first dialysis valve; closing the by-pass valve, the heater valve, the patient valve, the second dialysis valve and the drain valve; making the peristaltic pump rotate in a first rotation direction to pump priming fluid from the first compartment to the second compartment and from the first supply bag to the expansion chamber/s to perform a priming step.

In a 118$^{th}$ aspect according to aspect 3 or to aspect 109 when used with aspect 99, the method comprises or the control unit in configured to perform the following steps: opening the drain valve; closing the by-pass valve, the heater valve, the patient valve, the second dialysis valve and the first dialysis valve; making the peristaltic pump rotate in a second rotation direction to pump priming fluid from the second compartment to the first compartment and from the expansion chamber/s to the drain to perform a priming step.

In a 119$^{th}$ aspect according to aspect 3 or to aspect 109 when used with aspect 99, the method comprises or the control unit in configured to perform the following steps: opening the second dialysis valve; closing the by-pass valve, the heater valve, the patient valve, the drain valve and the first dialysis valve; making the peristaltic pump rotate in a first rotation direction to pump priming fluid from the first compartment to the second compartment and from the second supply bag to the expansion chamber/s to perform a priming step.

In a 120$^{th}$ aspect according to aspect 3 or to aspect 109 when used with aspect 99, the method comprises or the control unit in configured to perform the following steps: opening the first dialysis valve and the drain valve; closing the by-pass valve, the heater valve, the patient valve, the second dialysis valve; making the peristaltic pump rotate in a second rotation direction to pump priming fluid from the second compartment to the first compartment and from the first supply bag to the drain and performing a priming step.

In a 121$^{st}$ aspect according to aspect 3 or to aspect 109 when used with aspect 99, the method comprises or the control unit in configured to perform the following steps: opening the second dialysis valve and the drain valve; closing the by-pass valve, the heater valve, the patient valve, the first dialysis valve; making the peristaltic pump rotate in a second rotation direction to pump priming fluid from the second compartment to the first compartment and from the second supply bag to the drain and performing a priming step.

In a 122$^{rd}$ aspect according to aspect 3 or to aspect 109 when used with aspect 99, the method comprises or the control unit in configured to perform the following steps: opening the heater valve, the patient valve; closing the by-pass valve, the first dialysis valve, the drain valve, the second dialysis valve; making the peristaltic pump rotate in a first rotation direction to pump priming fluid from the first compartment to the second compartment and from the heater bag to the patient and performing a priming step.

In a 123$^{rd}$ aspect according to aspect 3 or to aspect 109 when used with aspect 99, the method comprises or the control unit in configured to perform the following steps: opening the heater valve, the patient valve, the by-pass valve, the first dialysis valve, the drain valve, the second dialysis valve; opening the yielding pump tube and performing a priming step.

A 124$^{th}$ aspect, which may be also independent, concerns a manifold assembly for a dialysis apparatus, wherein said manifold assembly comprises: a casing comprising a rigid shell and at least one soft membrane, the rigid shell and soft membrane delimiting at least a first fluid passage; the rigid shell comprising at least one port in fluid communication with said first fluid passage and with a second fluid passage; the at least one port having a seat; said at least one soft membrane facing the seat of said at least one port; the seat is configured for accommodating, at least partially, a respective occlusion element of a dialysis machine.

A 125$^{th}$ aspect concerns a dialysis apparatus comprising a dialysis machine and the manifold assembly of aspect 124, wherein the manifold assembly is mounted or mountable on the dialysis machine; the dialysis machine comprising at least one occlusion element; said occlusion element, when the manifold assembly is properly mounted on the dialysis device, faces the seat with the soft membrane there between; optionally the dialysis apparatus is an apparatus for extracorporeal treatment of blood; optionally the apparatus for extracorporeal treatment of blood comprises: a blood treatment device; an extracorporeal blood circuit coupled to the blood treatment device; a blood pump, a pump section of the extracorporeal blood circuit being configured to be coupled to the blood pump; optionally, a treatment fluid circuit operatively connected to the extracorporeal blood circuit and/or to the blood treatment device; optionally, the treatment fluid circuit comprises a dialysis line connected to a fluid chamber of the treatment unit and, optionally, a fluid evacuation line connected to said fluid chamber; optionally, the treatment fluid circuit comprises an infusion circuit comprising one or more infusion lines of a replacement fluid; wherein the manifold assembly may be part of the extracorporeal blood circuit or of the treatment fluid circuit.

In a 126$^{th}$ aspect according to any of aspects 24, 25, 29, 30, 35, 36, 40, 41, 45, 46, 51, 52, 91, 92, 98, 99, 108, 109 and 125, the occlusion element comprises a plunger and an actuator; wherein the actuator is configured to move the plunger between a retracted position, in which the plunger is spaced from the soft membrane and the port is open, and a forward position, in which the plunger is at least in part accommodated in the seat and the soft membrane is trapped between said plunger and said seat to close the port; optionally the actuator is a stepper motor or a linear actuator.

In a 127$^{th}$ aspect according to aspect 126, the soft membrane is configured to be deformed by the plunger, when said plunger is accommodated, at least in part, in the seat, to close the port.

In a 128$^{th}$ aspect according to aspect 127, the seat comprises an edge, optionally a circular edge, and, when the plunger is at least in part accommodated in the seat, the soft membrane is trapped between said plunger and the edge.

In a 129$^{th}$ aspect according to aspect 126 or 127 or 128, the occlusion element comprises a membrane tensioner configured to raise the soft membrane away from the seat when the plunger goes back to the retracted position and to counteract a possible negative pressure tending to keep the port closed; optionally the membrane tensioner is of mechanical type.

In a 130$^{th}$ aspect according to aspect 129, the membrane tensioner comprises a tensioning plunger connected to the actuator of the plunger or to an auxiliary actuator; wherein the actuator, or the auxiliary actuator, is configured to move the tensioning plunger between a retracted position, in which the tensioning plunger is spaced from the soft membrane, and a forward position, in which the tensioning plunger engages the soft membrane at locations other than the seat, optionally other than the edge, to move away the soft membrane from the seat and to stretch said soft membrane above the seat; optionally the tensioning plunger is positioned around the plunger; optionally the tensioning plunger comprises a substantially cylindrical wall; optionally the tensioning plunger is coaxial to the plunger.

In a $131^{st}$ aspect according to aspect 130, the tensioning plunger comprises at least one arched wall, optionally a plurality of arched walls; wherein at least one window is delimited by the arched wall or a plurality of windows are delimited between said arched walls; optionally, the tensioning plunger comprises two arched walls and two windows.

In a $132^{rd}$ aspect according to aspect 130 or 131, the tensioning plunger is in the retracted position when the plunger is in the forward position and the tensioning plunger is in the forward position when the plunger is in the retracted position.

In a $133^{rd}$ aspect according to aspect 130 or 131 or 132, the occlusion element comprises a shaft having a distal end carrying the plunger; the tensioning plunger is mounted on said shaft and is axially movable along said shaft; optionally the tensioning plunger is coaxial to said shaft; optionally the actuator is connected to the shaft to move said shaft.

In a $134^{th}$ aspect according to any of aspects 130 to 133, the locations other than the edge comprise an auxiliary edge spaced from the edge, wherein the auxiliary edge is raised with respect to the edge and extends in part around the seat, to keep the port open when the tensioning plunger is in the forward position; optionally the auxiliary edge is arch shaped or comprises at least one arch shaped part, optionally a plurality of arch shaped parts, wherein at least one radial opening is delimited by the arch shaped part or a plurality of radial openings are delimited between said arch shaped parts.

In a $135^{th}$ aspect according to any of aspects 130 to 134, the port comprises a shaped member protruding from a bottom surface of the rigid shell, wherein the seat is fashioned in said shaped member.

In a $136^{th}$ aspect according to aspect 135, the shaped member comprises the edge and the auxiliary edge.

In a $137^{th}$ aspect according to aspect 135 or 136, the shaped member is cylindrical or substantially cylindrical.

In a $138^{th}$ aspect according to any of aspects 135 to 137 the shaped member delimits a central cavity, wherein the edge delimits an upper part of said central cavity.

In a $139^{th}$ aspect according to aspect 134, when the tensioning plunger is in forward position, the wall or walls of the tensioning plunger are placed close to the auxiliary edge.

In a $140^{th}$ aspect according to aspect 135, when the tensioning plunger is in the forward position, the shaped member is at least in part positioned inside the tensioning plunger and the wall or walls of the tensioning plunger surround/s the auxiliary edge.

In a $141^{st}$ aspect according to aspect 131 and 134, when the tensioning plunger is in the forward position, the at least one arched wall of the tensioning plunger is placed close to the at least one arch shaped part of the auxiliary edge, such that the at least one window faces radially the at least one radial opening; optionally, each arched wall of the tensioning plunger is placed radially outside a respective arch shaped part of the auxiliary edge, such that each window faces radially a respective radial opening.

In a $142^{rd}$ aspect according to aspect 131 and 134, the arch shaped parts and the arched walls are equal in number.

In a $143^{rd}$ aspect according to any of aspects 130 to 142, the occlusion element comprises a reverse mechanism connecting the tensioning plunger and the plunger, wherein the reverse mechanism is configured to move the plunger in an opposite direction with respect to a moving direction of the tensioning plunger when the plunger or the tensioning plunger is moved by the actuator.

In a $144^{th}$ aspect according to aspect 143, the reverse mechanism comprises a rocker lever hinged to the plunger, to the tensioning plunger and to a stationary part of the dialysis machine or of the cycler, such that the tensioning plunger moves axially in a first direction when the shaft is moved axially in a second direction opposite the first direction; optionally the rocker lever is hinged to the shaft of the plunger.

In a $145^{th}$ aspect according to aspect 144, a first end of the rocker lever is hinged to the plunger, optionally to the shaft, a second end of the rocker lever is hinged to the tensioning plunger and a middle portion of the rocker lever is hinged to the stationary part.

In a $146^{th}$ aspect according to aspect 143, the reverse mechanism comprises a threaded coupling between the shaft and the tensioning plunger, such that the tensioning plunger moves axially in a first direction when the shaft is moved axially in a second direction opposite the first direction.

In a $147^{th}$ aspect according to aspect 146, the motor comprises a rotatable shaft and the rotatable shaft is coupled to the shaft of the plunger through a threaded coupling; the threaded coupling between the shaft and the tensioning plunger is left hand, the threaded coupling between the rotatable shaft and the shaft is a right end (or vice versa).

In a $148^{th}$ aspect according to any of aspects 126 to 147, the occlusion element comprises a damping and/or resilient element coupled to the plunger; optionally the damping and/or resilient element is placed between a distal end of a shaft carrying the plunger and said plunger.

A $149^{th}$ aspect concerns a method for calibrating a peristaltic pump in a dialysis apparatus, optionally a peritoneal dialysis apparatus or an apparatus for extracorporeal treatment of blood; wherein the dialysis apparatus comprises a dialysis machine or a cycler, according to one or more of the previous or following aspects, and a manifold assembly, according to one or more of the previous or following aspects.

A $150^{th}$ aspect concerns a dialysis apparatus, optionally a peritoneal dialysis apparatus or an apparatus for extracorporeal treatment of blood, comprising a dialysis machine or a cycler, according to one or more of the previous or following aspects, and a manifold assembly, according to one or more of the previous or following aspects; wherein a control unit of the dialysis machine or of the cycler is operatively connected at least to the peristaltic pump and to the pressure transducer and is configured and/or programmed to calibrate the peristaltic pump.

In a $151^{st}$ aspect according to aspect 149 or 150, the method comprises or the control unit is configured and/or programmed to perform the following steps:

i. rotating the peristaltic pump of a predetermined rotation to pump a liquid from the fluid source into the second compartment and raise a level of the liquid in the second compartment to compress air in the air buffer volume;

ii. measuring pressure of air in the air buffer volume;

iii. calculating, from the measured pressure of air in the air buffer volume, a variation of liquid volume in the second compartment due to the rotation of the peristaltic pump;

iv. calculating, from the variation of liquid volume and the predetermined rotation, a stroke liquid volume of the peristaltic pump.

In a $152^{nd}$ aspect according to aspect 151 rotating the peristaltic pump of a predetermined rotation comprises: rotating the peristaltic pump for a plurality of revolutions or fractions of revolutions such that a pressing element of the peristaltic pump or one of a plurality of pressing elements of the peristaltic pump is in a same predetermined position at a start and at an end of the rotation.

In a $153^{rd}$ aspect according to aspect 152, the peristaltic pump comprises an encoder operatively connected to the control unit to detect position and movement of the pressing element or elements of the peristaltic pump.

In a $154^{th}$ aspect according to aspect 153, the control unit is configured and/or programmed to detect the predetermined position through the encoder.

In a $155^{th}$ aspect according to any of aspects 151 to 154, the peristaltic pump comprises two pressing elements angularly spaced of 180° and the predetermined rotation comprises "n" half-revolutions of the peristaltic pump; optionally "n" is an integer between five and ten; optionally a rotational speed of the peristaltic pump is between 3 rpm and 8 rpm.

In a $156^{th}$ aspect according to any of aspects 150 to 155, the yielding pump tube is shaped as a loop comprising a rounded part and two straight parts, wherein the pressing element/s squeeze/s the rounded part during rotation.

In a $157^{th}$ aspect according to aspect 156 when according to aspect 152, the predetermined position is at, or close to, a portion between the rounded part and one of the two straight parts.

In a $158^{th}$ aspect according to any of aspects 151 to 157, measuring pressure of air in the air buffer volume comprises: measuring an initial pressure before air compression and measuring a final pressure after air compression.

In a $159^{th}$ aspect according to aspect 158, the initial pressure is about 0 mmHg.

In a $160^{th}$ aspect according to aspect 158 or 159, the final pressure is about 400 mmHg.

In a $161^{st}$ aspect according to any of aspects 151 to 160, the level of the liquid is raised starting from a first level; wherein, at the end of the predetermined rotation, the liquid is at a second level.

In a $162^{rd}$ aspect according to aspect 161 when according to any of aspects 158 to 159, the variation of liquid volume is calculated as a function of an initial air volume above the first level and of the initial pressure and the final pressure.

In a $163^{rd}$ aspect according to aspect 162 and aspect 155, the stroke liquid volume is a ratio between the variation of liquid volume and a number of half-revolutions of the peristaltic pump contained in the predetermined rotation.

In a $164^{th}$ aspect according to any of aspects 161 to 163 and to aspect 96, the at least one level sensor comprises a low level sensor and the first level of liquid is obtained by rotating the peristaltic pump until sensing a low liquid level through the low level sensor and further rotating the peristaltic pump of a predetermined angle to pump an extra volume of liquid above the low liquid level in the second compartment.

In a $164^{th}$ bis aspect according to aspect 164, rotating the peristaltic pump until sensing the low liquid level comprises: rotating the peristaltic pump in a first rotation direction to pump fluid from the first compartment to the second compartment until sensing the low liquid level for a first time and stopping the peristaltic pump; rotating the peristaltic pump in a second rotation direction to bring the liquid level below the low liquid level and stopping the peristaltic pump; rotating again the peristaltic pump in the first rotation direction to reach again the low liquid level and keep on rotating the peristaltic pump to pump the extra volume of liquid.

In a $165^{th}$ aspect according to aspect 164 and aspect 152, the predetermined position of the pressing element is the position at the end of the further rotation of the predetermined angle; optionally, the control unit is configured and/or programmed to set the predetermined position of the pressing element as the position at the end of the further rotation of the predetermined angle and the peristaltic pump is rotated of said predetermined rotation starting from the predetermined position of the pressing element corresponding to said first level, optionally, an air valve connected to the air buffer volume is open before reaching the predetermined position and said air valve is closed once reached to predetermined position and during the following compression.

In a $166^{th}$ aspect according to aspect 164 or 165, the first level is the level reached at the end of the further rotation of the predetermined angle.

In a $167^{th}$ aspect according to any of aspects 164 to 166, the predetermined angle is between 900 and 120°.

In a $168^{th}$ aspect according to any of aspects 164 to 167, a first volume is delimited in the second compartment below the low level sensor; optionally said first volume is between 5 ml and 15 ml.

In a $169^{th}$ aspect according to any of aspects 164 to 168 and aspect 162 or 163, the initial air volume is a difference between a volume of air above the low liquid level and the extra volume of liquid.

In a $170^{th}$ aspect according to any of aspects 165 or 166 to 169 when according to aspect 165, the at least one level sensor comprises a high level sensor and a high liquid level is sensed through the high level sensor and the rotation of the peristaltic pump is stopped when the pressing element is in the predetermined position for a first time after sensing the high liquid level.

In a $171^{st}$ aspect according to aspect 170, a second volume is delimited in the second compartment between the low level sensor and the high level sensor.

In a $172^{nd}$ aspect according to aspect 171, the second volume is between two and four times a nominal stroke liquid volume of the peristaltic pump, optionally between 15 ml and 25 ml.

In a $173^{rd}$ aspect according to aspect 172, a third volume is delimited in the second compartment above the high level sensor.

In a $174^{th}$ aspect according to aspect 173, the third volume is between 10 ml and 20 ml.

In a $175^{th}$ aspect according to any of aspects 170 to 174, the method comprises or the control unit is configured and/or programmed to perform the following step: after stopping the rotation of the peristaltic pump and before taking the final pressure, waiting for a stabilizing time and keeping on measuring pressure, to check for possible leakages.

In a $176^{th}$ aspect according to aspect 150 or to any of aspects 151 to 175 when according to aspect 150, the casing comprises a breathable membrane configured to put into communication the pressure transducer with the air buffer volume.

In a $177^{th}$ aspect according to aspect 176, the dialysis machine or the cycler further comprises an auxiliary chamber in fluid communication with the air buffer volume, through the breathable membrane, and with the pressure transducer.

In a 178th aspect according to aspect 177, a fourth volume of the auxiliary chamber is between 20 ml and 30 ml; optionally a sum of the second, third and fourth volume is between 50 ml and 70 ml.

In a 179th aspect according to any of aspects 151 to 178, calculation of the stroke liquid volume through steps i. to iv. is executed consecutively a plurality of times, optionally two to five times, and an average stroke liquid volume is determined.

The at least one expansion chamber which is configured to attenuate pressure pulsations from the peristaltic pump, attenuates the effects of the peristalsis of the peristaltic pump with a positive effect on the patient comfort.

The presence of the air buffer volume assures the removal of gas bubbles potentially present in the solutions before administration to the patient.

The connection of the air buffer volume with the pressure transducer allows a monitoring of the pressure values within the second compartment connected to the patient line tube, with a contextual interface with the air pump that can regulate the fluid level of the second compartment accordingly to the feedback provided by the fluid level sensors.

The mentioned soft plastic sheet interfacing with the displacement sensor of the cycler allows detection of potential occurrence of extreme negative pressure values in the first compartment connected to the drain and heater bag.

The shape of the casing of the manifold assembly provides an improved usability characterized by a "one hand first handling step" for mounting the device on the cycler.

The whole design of the manifold assembly is also compatible with an user friendly interface with the cycler's hardware components.

The structure of the ports of the casing and occlusion elements of the cycler or dialysis machine ensure accurate and punctual closing and opening movements of the valves.

The yielding pump tube coupled to the peristaltic pump together with the calibration of the assembly comprising the yielding pump tube and the peristaltic pump allows an accurate and simple control of the fluids flows and an enhanced monitoring of the effectiveness of the dialysis treatment.

BRIEF DESCRIPTION OF THE DRAWINGS

FIG. 5 is a schematic sectional view of a portion of the side view of FIG. 4;

FIGS. 6A and 6B are schematic sectional views of another portion of the assembly taken along section line VI-VI of FIG. 3;

FIGS. 12 to 15 are flow diagrams illustrating the configurations of FIGS. 8 to 11;

FIG. 18 is a flow diagram illustrating the configuration of FIG. 17;

DETAILED DESCRIPTION

Embodiment 1

Figure 1:
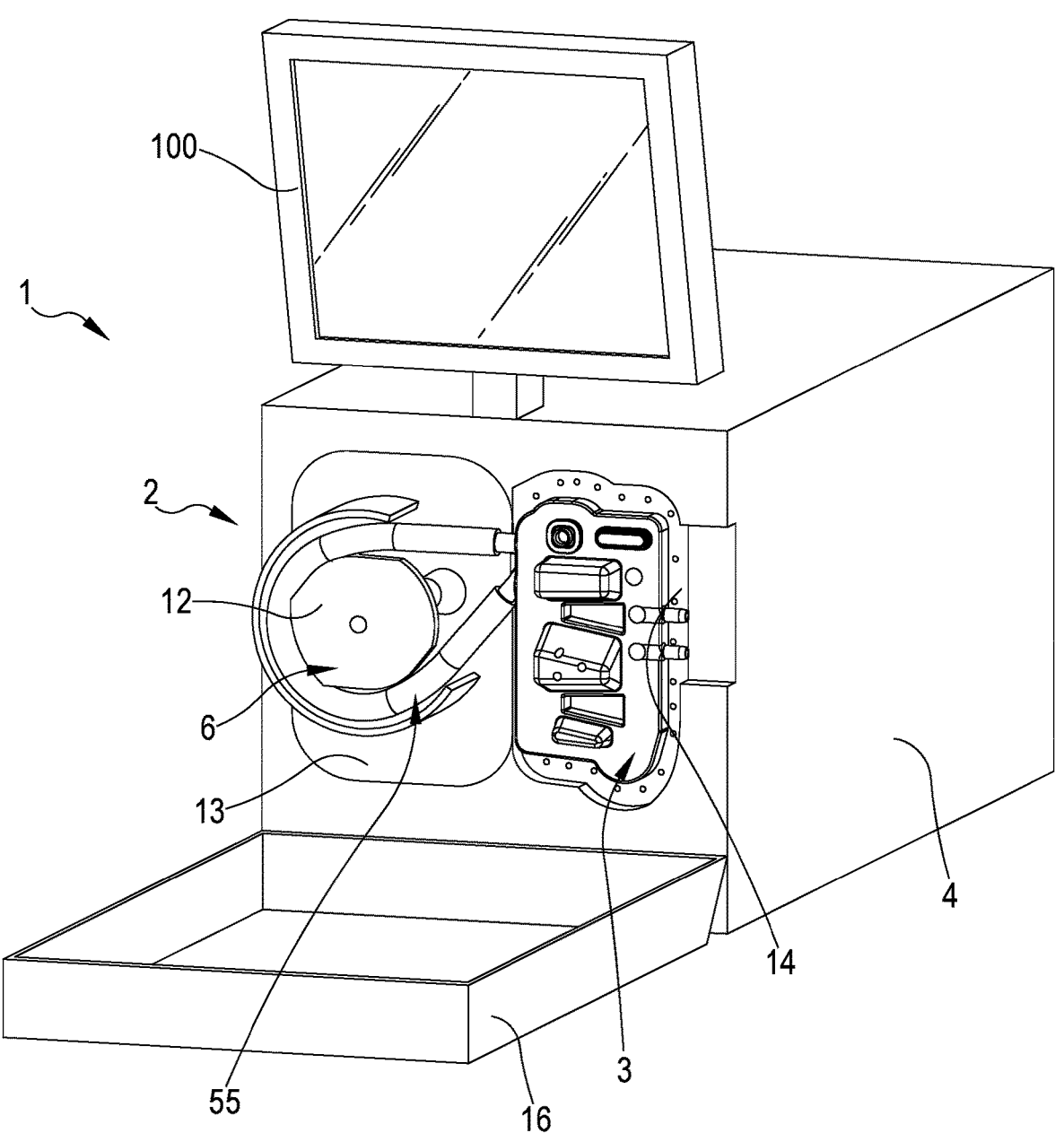
FIG. 1 is a perspective view of one embodiment for an automated peritoneal dialysis apparatus ("APD") of the present disclosure.

Referring now to the FIGS. 1 to 15, an embodiment of a peritoneal dialysis apparatus 1 (APD) comprises a cycler 2 and a manifold assembly 3 (FIGS. 2 and 3) that organizes tubing and performs many functions discussed herein.

The cycler 2 comprises a box 4 housing all the mechanical and electronical parts of the cycler 2. The cycler 2 comprises an electronic control unit 5 (FIG. 4), a roller peristaltic pump 6 (FIG. 1), a plurality of occlusion elements 7, a first or high level sensor 8 and a second or low level sensor 9, a pressure transducer 10 and an air pump 11 (schematically illustrated in FIG. 4). The cycler 2 may also comprise a heater, not shown.

Figure 3:
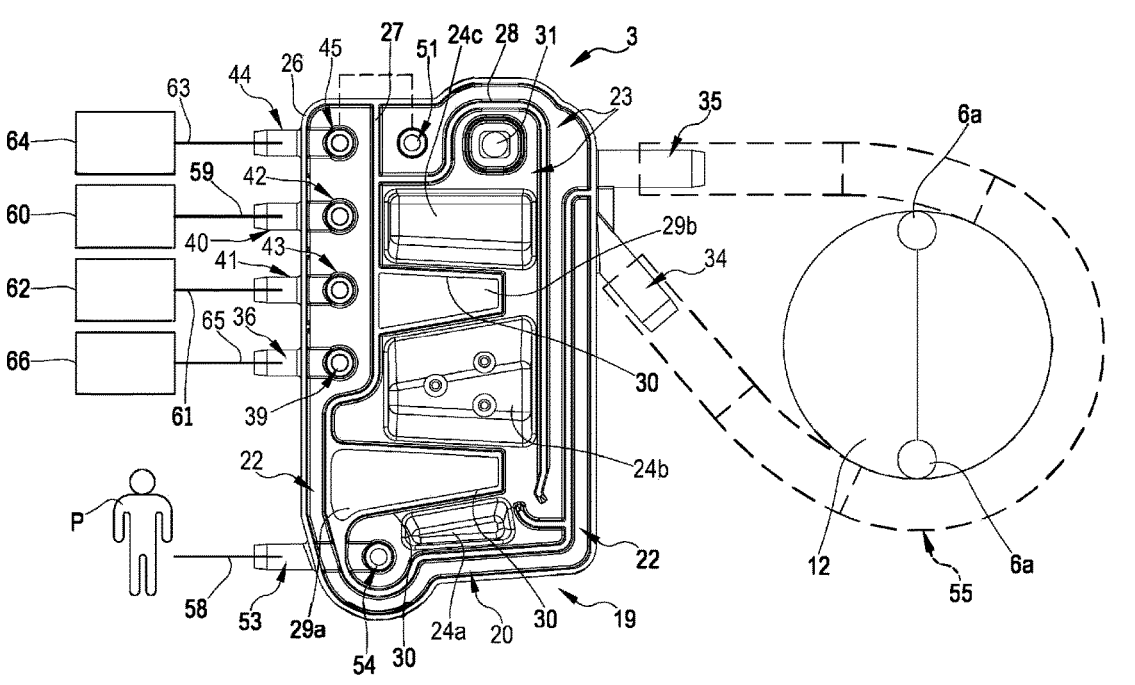
FIG. 3 is a rear view of the manifold assembly of FIG. 2 with some parts removed to illustrate the interior and some other parts schematically represented.
Figure 25:
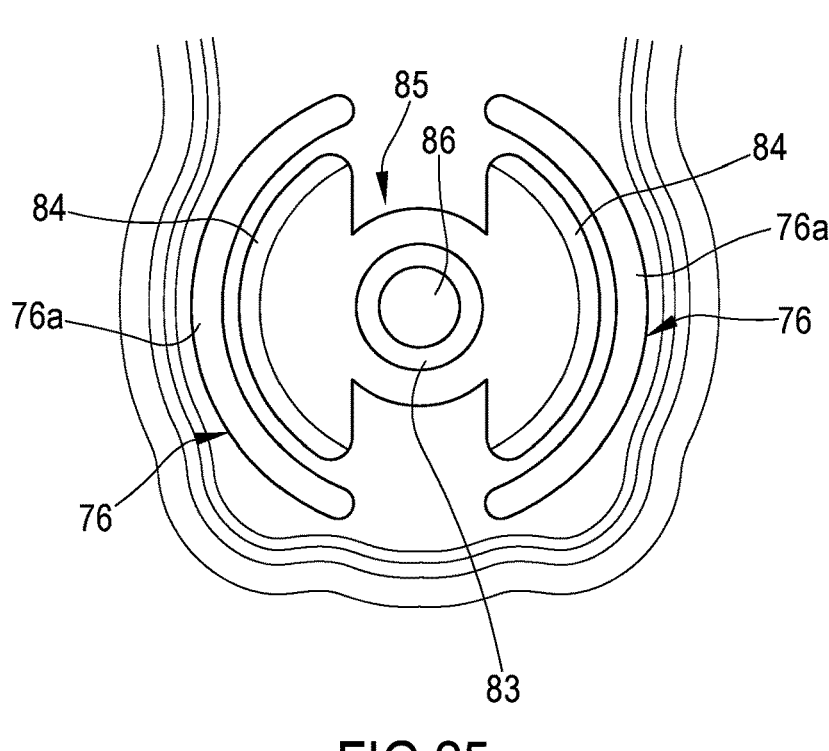
FIG. 25 is a schematic top view of the valve of FIG. 20A and the member of FIG. 24.

The peristaltic pump shown in FIGS. 3 and 25 comprises two pressing rollers 6a angularly spaced of 180°.

A motor, not shown, of the peristaltic pump 6 is housed in the box 4 and a rotor 12 of the peristaltic pump 6 is positioned on a front panel 13 of the box 4 (FIG. 1).

A site 14 of the front panel 13 next to the rotor 6 is configured to retain in removable manner the manifold assembly 3 on said front panel 13. The site 14 may comprise retaining elements configured to be coupled to the manifold assembly 3 and/or the manifold assembly 3 comprises hooking elements configured to hook, in removable manner, said disposable assembly 3 to the front panel 13 of the cycler 2.

The occlusion elements 7 (FIG. 4) protrude from the front panel at the site 14. Each occlusion element 7 comprises a plunger 15 (FIGS. 6A and 6B) moved by a respective actuator, not shown, housed in the box 4. The actuator is configured to move the plunger 15 between a retracted position (FIG. 6A) and a forward position (FIG. 6B), as will be discussed herein.

The cycler 2 comprises a lid 16 (FIGS. 1 and 4) movable between a closed position, in which the lid 16 covers the front panel 13, and an open position, in which the lid 16 is spaced from the front panel 13 to allow a user to access to said front panel 13. The lid 16 of the embodiment of the attached Figures is hinged to the box 4 and may be rotated between the open and the closed position. For sake of simplicity, elements detailed below and belonging to the lid 16 have not been depicted in FIG. 1.

When the manifold assembly 3 is properly mounted on the site 14 of the cycler 2 and the lid 16 is in the closed position, said manifold assembly 3 is closed between the front panel 13 and the lid 16.

Figure 4:
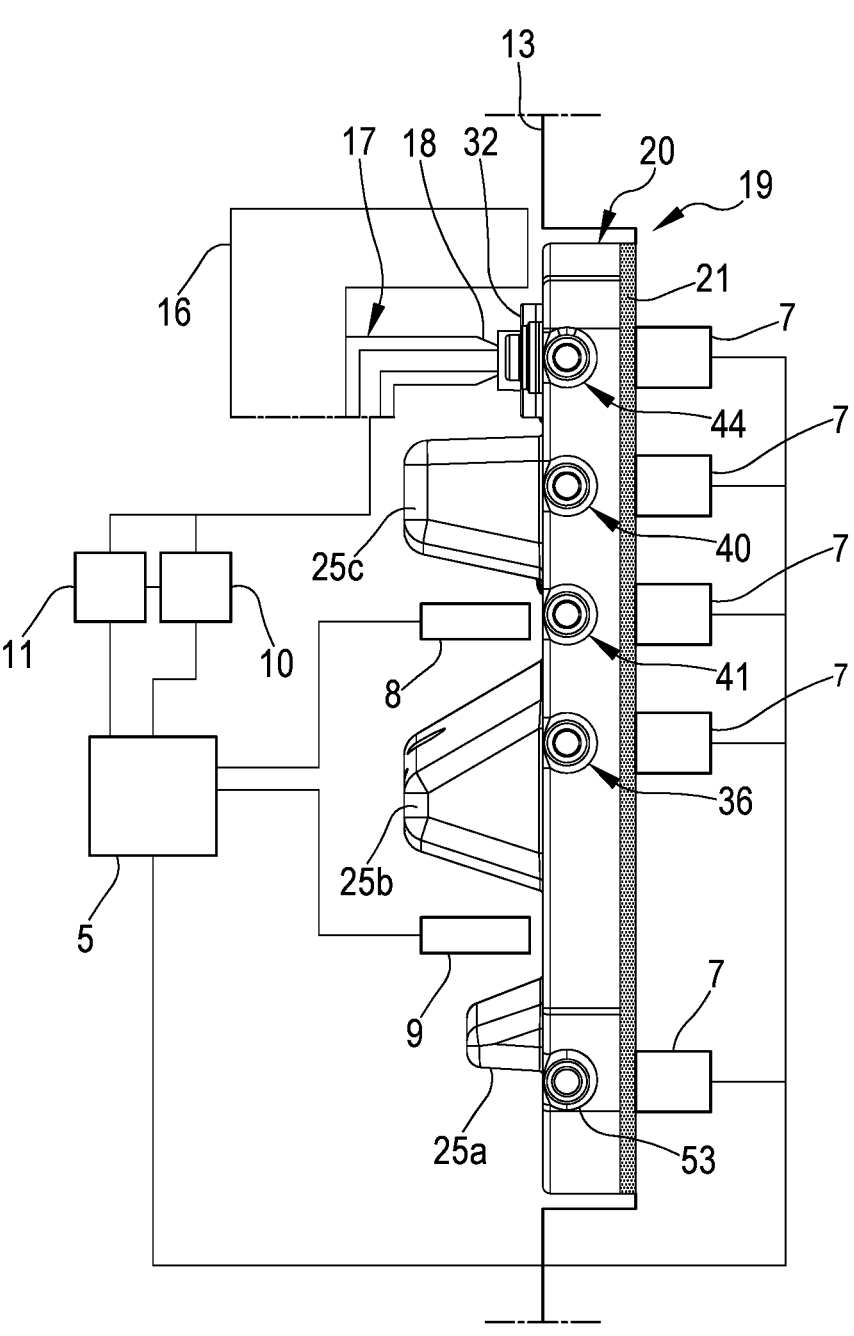
FIG. 4 is a side view of the manifold assembly of FIG. 2.

The first level sensor 8 and the second level sensor 9 are installed on the lid 16 and protrude from a side of the lid 16 configured to face the front panel 13 and/or the manifold assembly 3 when the lid 16 is in the closed position (FIG. 4). The illustrated level sensors 8, 9 are capacitive sensors. In other embodiments, not shown in the attached Figures, the level sensors 8, 9 may be ultrasonic sensors or other type of sensors and/or may be installed on the front panel of the box 4.

An air conduit 17 is mounted on the lid 16 and comprises a coupling end 18. The coupling end 18 is configured to face the manifold assembly 3 when the lid 16 is in the closed position (FIGS. 4 and 5), as will be discussed herein. The air conduit 17 is in air communication with the pressure transducer 10 and the air pump 11. The pressure transducer 10 and the air pump 11 may be installed in the lid 16 or in the box 4.

The control unit 5, schematically shown in FIG. 4, is operationally connected to the motor of the peristaltic pump 6, to the actuators of the occlusion elements 7, to the pressure transducer 10 and the air pump 11, to the first level sensor 8 and second level sensor 9, to the heater and to any other device or sensor of the cycler 2 and is configured/programmed to control operation of the peritoneal dialysis apparatus 1.

The control unit may be also connected to a display, a keyboard or a touch screen 100 configured to show working parameters of the apparatus 1 and/or to allow a user to set up the apparatus 1 (FIG. 1).

The lid 16 and/or the front panel 13 of the box 4 may also comprise further elements, not shown, configured to manage and route tubing of the manifold assembly 3.

The manifold assembly 3 for the peritoneal dialysis apparatus 1 comprises a disposable casing 19 comprising a rigid molded plastic rigid shell 20, e.g. made of PETG (polyethylene terephthalate glycol-modified) polymer (FIGS. 2, 3 and 4), and a plastic sheet 21, e.g. a polyvinyl chloride soft sheet (FIG. 4). The rigid molded plastic rigid shell 20 delimits a front and sides of the casing 19 and the plastic sheet 21 is a back of the casing 19 (FIG. 4).

Figure 2:
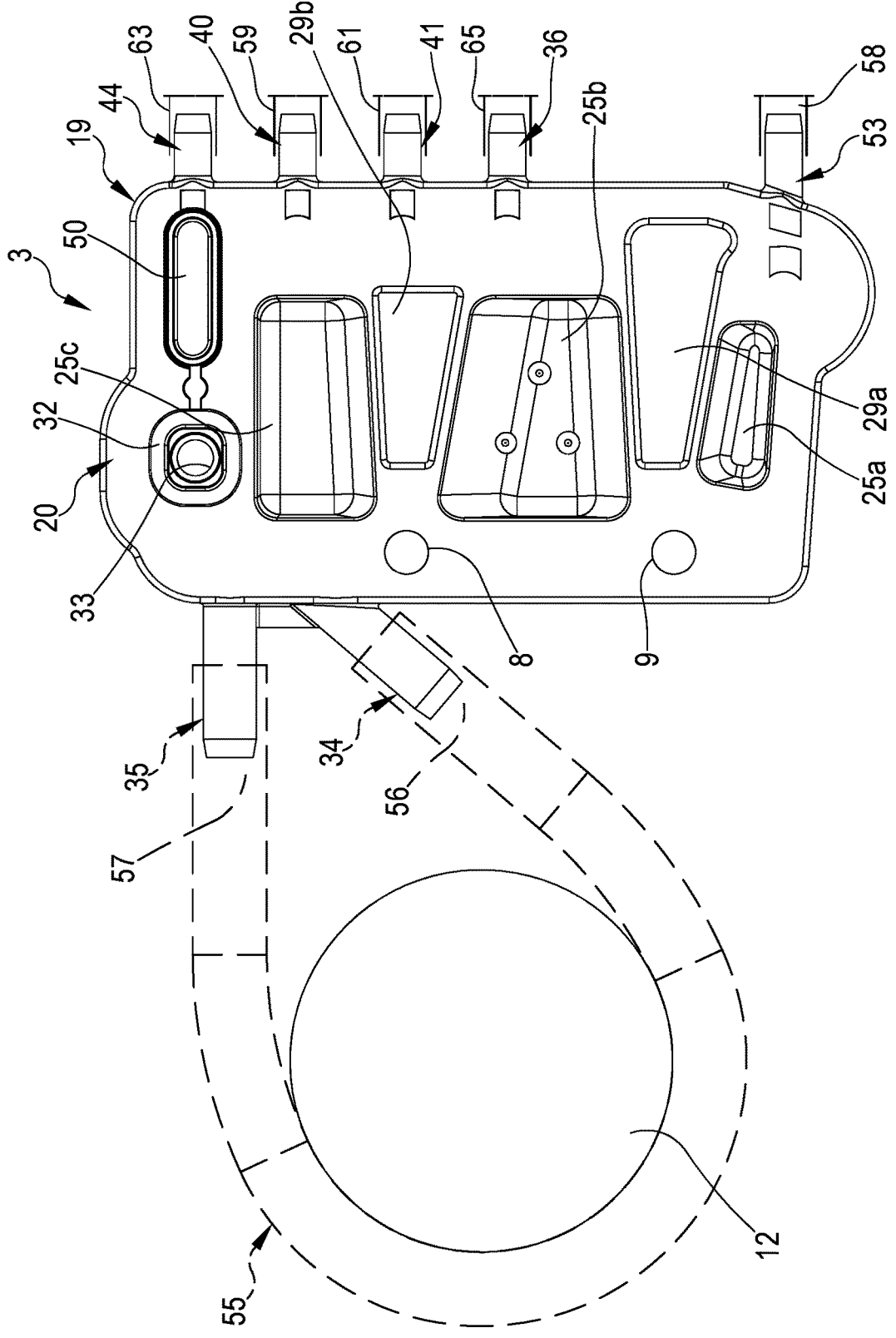
FIG. 2 is a front view of one embodiment for a manifold assembly of the APD apparatus of the present disclosure.

The plastic rigid shell 20 has a substantially flattened shape and comprises septa and recesses on the inner side of the casing 19. Said septa delimit internally a first compartment 22 and a second compartment 23 for fresh and spent dialysis fluid (FIG. 3). Said recesses delimit internally respective three expansion chambers 24a, 24b, 24c and externally, on the front of the casing 19, respective three protrusions 25a, 25b, 25c (FIGS. 2 and 3).

In a front view or back view, the plastic rigid shell 20 and the casing 19 have a substantially rectangular outline with two long sides and two short sides. When the casing 19 is properly mounted on the cycler 2, the two long sides are vertical.

The first compartment 22 is delimited by an outer septum 26 positioned on a peripheral border of the plastic rigid shell 20 and by a first inner septum 27. Referring to the back view of FIGS. 3, 8, 9, 10, 11, the first inner septum 27 has a first extremity connected to the outer septum 26 on the top short side of the plastic rigid shell 20 and a second extremity connected to the outer septum 26 on the right long side of the of the plastic rigid shell 20.

The first inner septum 27 has a substantially U-shape and develops substantially parallel to the left long side, to the bottom short side and to the right long side of the plastic rigid shell 20. The first compartment 22 is a U-shaped first elongated passage.

The second compartment 23 is delimited by the first inner septum 27 and by a portion of the outer septum 26 not delimiting the first compartment 22, such that the second compartment 23 is partly surrounded by the U-shaped first compartment 22.

A second inner septum 28 is positioned inside the second compartment 23 to create a route in the second compartment 23. The second inner septum 28 has a first extremity connected to the first inner septum 27 at a location close to the first extremity of said first inner septum 27 and a second free extremity positioned close to a lower right corner of the plastic rigid shell 20.

Referring to the back view of FIGS. 3, 8, 9, 10, 11, the second inner septum 28 has a substantially inverted L-shape and develops substantially parallel to the top short side and to the right long side of the plastic rigid shell 20. Therefore, the second compartment 23 comprises an inverted L-shaped second elongated passage.

A long stretch of the inverted L-shaped second elongated passage is parallel to a right long stretch of the U-shaped first elongated passage. The second compartment 23 comprises a main central part divided, in part, from the second elongated passage by the second inner septum 28. The second elongated passage has a second extremity communicating with the main central part.

The three expansion chambers 24a, 24b, 24c are fashioned in the main central part of the second compartment 23 and each expansion chamber 24a, 24b, 24c has a depth greater than a depth of a remaining part of the second compartment 23.

Two through apertures 29a, 29b (FIGS. 2 and 3) pass through the plastic rigid shell 20 and the main central portion of the second compartment 23. These two through apertures are surrounded and delimited by respective further septa 30 connected to the first inner septum 27 Therefore, also these further septa 30 delimit the second compartment 23.

A first aperture 29a and a second aperture 29b are positioned between two of said three of expansion chambers 24a, 24b, 24c. A first expansion chamber 24a of the three expansion chambers 24a, 24b, 24c is close to the bottom short side of the casing 19 and to a short stretch of the U-shaped first elongated passage; a second expansion chamber 24b of the three expansion chambers 24a, 24b, 24c is placed between the first aperture 29a and the second aperture 29b; a third expansion chamber 24c of the three expansion chambers 24a, 24b, 24c is placed above the second aperture 29b.

An inner volume delimited in the second compartment 23 is greater than an inner volume delimited in the first compartment 22. For instance, the inner volume of the second compartment 23 is about 55 m³ and the inner volume of the first compartment 22 is about 14 m³.

A hole 31 (FIG. 3) is fashioned in the front of the plastic rigid shell 20 located between the third expansion chamber 24c and the second inner septum 28. A rigid plastic frame 32 supporting a breathable membrane 33 (FIG. 2) is joined, by welding or gluing, to an edge of the hole 31. The breathable membrane 33 may be of PTFE (polytetrafluoroethylene).

When the assembly 3 is properly mounted on the cycler 2, an upper part of the second compartment 23 provided with the breathable membrane 33 delimits an air buffer volume, as will be discussed herein.

The plastic sheet 21 (FIG. 4) is welded or glued to the plastic rigid shell 20 The plastic sheet 21 is joined to the outer septum 26, the first inner septum 27, the second inner septum 28 and to the further septa 30, to seal the first compartment 22 and the second compartment 23.

The plastic rigid shell 20 comprises a first pump port 34 comprising a hollow cylinder protruding from a right side (in FIGS. 3 and 8-11) of the casing 19. The first pump port 34 is in fluid communication with the first compartment 22. The first pump port 34 opens inside the first compartment 22 at an extremity of the right long stretch of the U-shaped first elongated passage.

The plastic rigid shell 20 comprises a second pump port 35 comprising a hollow cylinder protruding from the right side (in FIGS. 3 and 7-10) of the casing 19. The second pump port 35 is in fluid communication with the second compartment 23. The second pump port 35 opens inside the second compartment 23 at a first extremity of the second elongated passage.

The first pump port 34 and the second pump port 35 are close to each other but separated by the first inner septum 27. The hollow cylinders defining the first pump port 34 and the second pump port 35 diverge from each other away from the casing 19.

The plastic rigid shell 20 comprises a drain port 36 comprising a hollow cylinder 37 protruding from the left side (in FIGS. 3 and 7-10) of the casing 19.

The hollow cylinder 37 of the drain port 36 passes through the outer septum 26 such that said drain port 36 is in fluid communication with the first compartment 22.

The drain port 36 comprises a short hollow barrel 38 connected to the hollow cylinder 37. A central axis of the hollow cylinder 37 is perpendicular to a main axis of the hollow barrel 38 and the cavities delimited inside the hollow cylinder 37 and the hollow barrel 38 are in fluid communication with each other. The hollow barrel 38 protrudes from a bottom surface of the first compartment 22 and opens inside the first compartment 22 (FIGS. 6A and 6B).

The hollow barrel 38 is shorter than the adjacent outer septum 26 (as shown in FIGS. 6A and 6B), than the first inner septum 27, than the second inner septum 28, than the further septa 30, such that the plastic sheet 21 is spaced from an edge of the hollow barrel 38, when said plastic sheet 21 is not deformed, as shown in FIG. 6A.

As will be discussed herein, the edge of the hollow barrel 38 and a part of the plastic sheet 21 facing said edge form a drain valve 39 of the drain port 36.

The plastic rigid shell 20 further comprises a first dialysis port 40 and a second dialysis port 41. Each of these ports 40, 41 protrudes from the left side (in FIGS. 3 and 7-10) of the casing 19 and has the same structure as the drain port 36 detailed above (hollow cylinder 37 and hollow barrel 38).

The first dialysis port 40 and a second dialysis port 41 have a receptive first dialysis valve 42 and a respective second dialysis valve 43.

The plastic rigid shell 20 further comprises a heater port 44 which also protrudes from the left side (in FIGS. 3 and 7-10) of the casing 19 and is structurally similar to the drain port 36 detailed above (hollow cylinder 37 and hollow barrel 38). The heater port 44 has a heater valve 45. The heater port 44 is placed close to an upper left corner of the plastic rigid shell 20.

Figure 7:
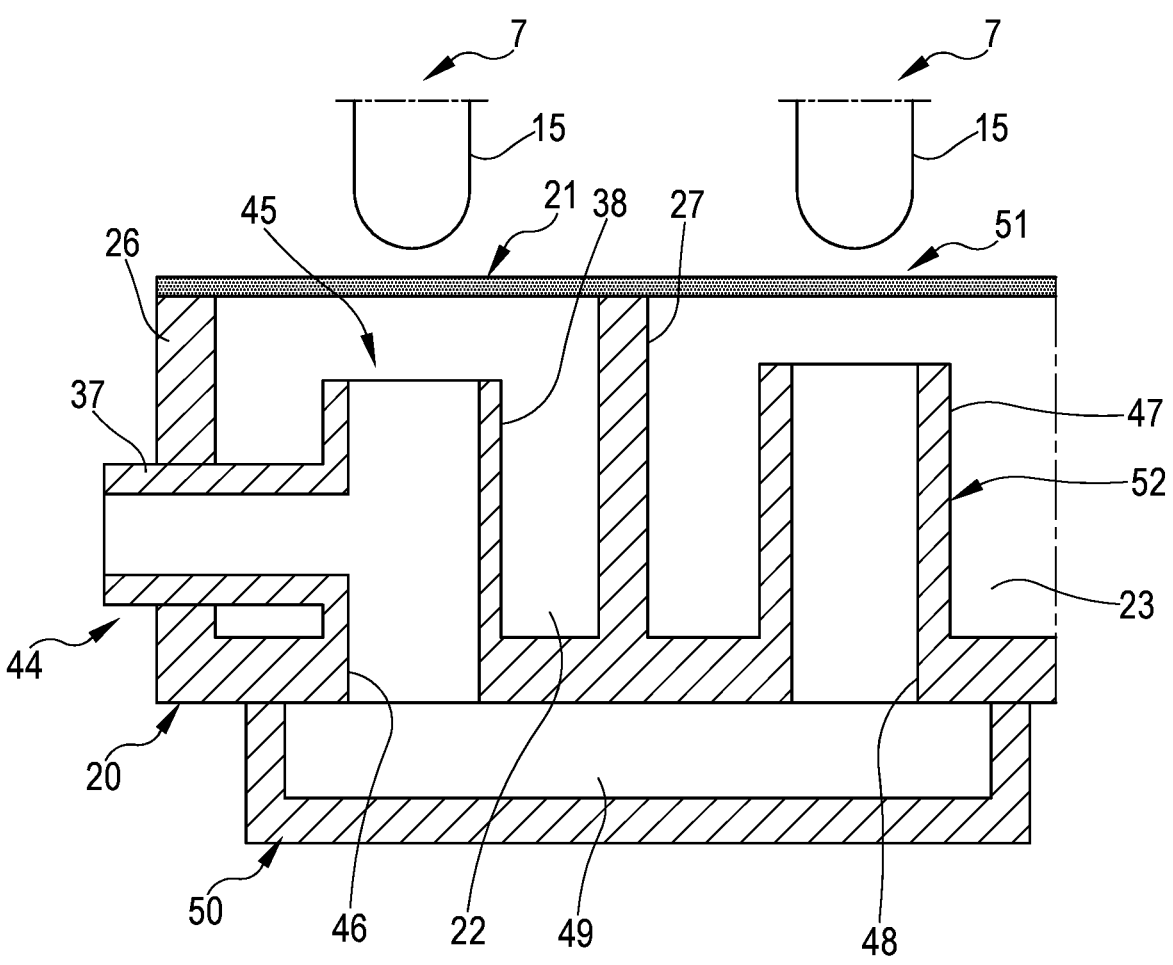
FIG. 7 is a schematic sectional view of another portion of the assembly taken along section line VII-VII of FIG. 3.

Differently from the drain port 36, from the first dialysis port 40 and from the second dialysis port 41, the hollow barrel 38 of the heater port 44 is also in fluid communication with an opening 46 fashioned through the front of the casing 19 (FIG. 7).

The plastic rigid shell 20 comprises a further hollow barrel 47 placed in the second compartment 23 and close to the hollow barrel 38 of the heater port 44. The first inner septum 27 is located between the further hollow barrel 47 and the hollow barrel 38.

The further hollow barrel 47 is in fluid communication with a further opening 48 fashioned through the front of the casing 19 (FIG. 7) and the opening 46 and the further opening 48 are connected by a by-pass channel 49 delimited by a cover 50 welded or glued to the front of the plastic rigid shell 20. The by-pass channel 49 is in fluid communication with the first compartment 22, with the second compartment 23 and with the heater line tube 63.

An edge of the further hollow barrel 47 and a part of the plastic sheet 21 facing said edge form a by-pass valve 51. The further hollow barrel 47 is part of a by-pass port 52 provided with the by-pass valve 51.

Figure 8:
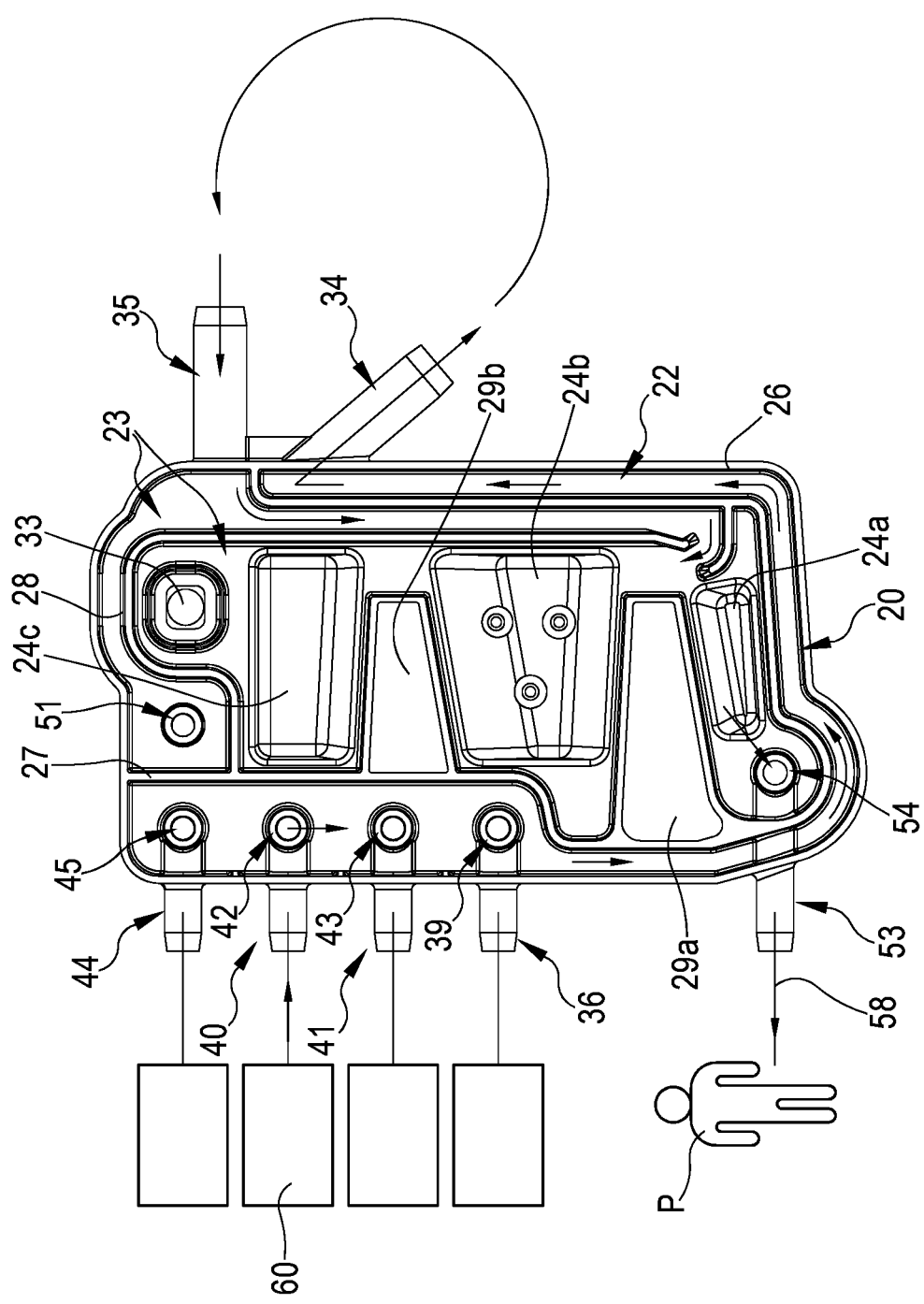
FIGS. 8 to 11 show the rear view of FIG. 3 illustrating respective configurations of the manifold assembly and related liquid flow paths.

The second inner septum 28 separates an area of the second compartment 23 with the hole 31 and the breathable membrane 33 from the by-pass valve 51 (FIGS. 3 and 8).

The plastic rigid shell 20 further comprises a patient port 53. The patient port 53 protrudes from the left side (in FIGS. 3 and 7-10) of the casing 19 and has the same structure as the drain port 36 detailed above (hollow cylinder 37 and hollow barrel 38).

The hollow cylinder 37 of the patient port 53 passes through the outer septum 26 and the first inner septum 27 such that said patient port 53 is in fluid communication with the second compartment 23 (FIG. 3). The patient port 53 has a patient valve 54.

All the valves (drain valve 39, first dialysis valve 42, second dialysis valve 43, heater valve 45, by-pass valve 51, patient valve 54) are structurally and functionally identical and, when the manifold assembly 3 is properly mounted on the cycler 2, they are each placed in front of a respective occlusion element 7 of the cycler 2. Each occlusion element 7 of the cycler 2 is configured to open or close the respective valve (FIGS. 6A and 6B). In other embodiments, not shown in the attached Figures, the occlusion element 7 may be installed on the lid 16 and the structure of the manifold assembly 3 is such to cooperate with said occlusion element 7 on the lid 16.

The hollow cylinders 37 of the heater port 44, the first dialysis port 40, the second dialysis port 41, the drain port 36 and the patient port 53 are parallel with respect to each other. In the embodiment of the attached Figures, when the manifold assembly 3 is properly mounted on the cycler 2, the heater port 44 is above the first dialysis port 40 which in turn is above the second dialysis port 41 which in turn is above the drain port 36 which in turn is above the patient port 53.

The first compartment 22 shaped like a U-shaped first elongated passage extends between the heater port 44 and the first end of the first pump port 34. The second elongated passage has a first extremity connected to the second pump port 35.

The manifold assembly 3 comprises a yielding pump tube 55 having a first end 56 connected to the first pump port 34 and to first compartment 22 and a second end 57 connected to the second pump port 35 and to the second compartment 23 (FIG. 1). The yielding pump tube 55 extends outside the casing 19 and is shaped as a loop or as an eyelet having an omega "0" shape to be placed in part around the rotor 12 of the peristaltic pump 6 of the cycler 2.

The manifold assembly 3 further comprises (FIG. 3): a patient line tube 58 having a first end connected to the patient port 53 and a second end connectable to a patient's peritoneal cavity; a first dialysis fluid line tube 59 having a first end connected to the first dialysis port 40 and a second end connected to a first supply bag 60; a second dialysis fluid line tube 61 having a first end connected to the second dialysis port 41 and a second end connected to a second supply bag 62; a heater line tube 63 having a first end connected to the heater port 44 and a second end connected to a heater bag 64; a drain fluid line tube 65 having a first end connected to the drain port 36 and a second end connected to a drain 66.

The patient line tube 58 may extend to a patient line connector, which may for example connect to a patient's transfer set leading to an indwelling catheter that extends to the patient's peritoneal cavity.

The first compartment 22, the yielding pump tube 55 and the second compartment 23 delimit together a fluid path extending between one of the first dialysis fluid line tube 59, second dialysis fluid line tube 61, heater line tube 63, drain fluid line tube 65 and the patient line tube 58, to allow fluid flow from one of the fluid line tubes to the patient line tube 58 or from the patient line tube 58 to one of the fluid line tubes when the peristaltic pump 6 of the cycler 2 is actuated.

The casing 19 of the manifold assembly 3 is mounted on the front panel 13 of the cycler 2, the yielding pump tube 55 is coupled to the rotor 12 and the first dialysis fluid line tube 59, second dialysis fluid line tube 61, heater line tube 63, drain fluid line tube 65 are properly arranged and connected to the respective first supply bag 60, second supply bag 62, heater bag 64 and drain 66. The patient line tube 58 is properly arranged and connected to the patient P. The heater bag 64 is coupled to the heater of the cycler 2.

The shape of the casing 19, with the three protrusions 25a, 25b, 25c and the two through apertures 29a, 29b, facilitate the user to grab the casing 19 and to mount the casing 19 on the cycler 2.

The user closes the lid 16 so that the first level sensor 8 and the second level sensor 9 are positioned in front of an external flat surface of the casing 19. The position of the first level sensor 8 and the second level sensor 9 when the lid 16 is closed is shown in FIG. 2 and FIG. 4. In FIG. 2 the positions of the first level sensor 8 and second level sensor 9 are schematically represented through dashed line circles.

The first level sensor 8 and the second level sensor 9 are placed one above the other. The first level sensor 8 is positioned between the third expansion chamber 24c and the second expansion chamber 24b. The second level sensor 9 is positioned between the second expansion chamber 24b and the first expansion chamber 24a.

When the lid 16 is closed, the coupling end 18 of the air conduit 17 is coupled to the rigid plastic frame 32 supporting the breathable membrane 33 (FIGS. 4 and 5) such that the coupling end 18 faces the breathable membrane 33. This way, the pressure transducer 10 and the air pump 11 of the cycler 2 are put into communication with the breathable membrane 33 and with the upper part of the second compartment 23, i.e. with the air buffer volume.

According to a method for controlling the peritoneal dialysis apparatus 1, the control unit 5 commands the actuators of the occlusion elements 7 to open or close the drain valve 39, first dialysis valve 42, second dialysis valve 43, heater valve 45, by-pass valve 51 and patient valve 54 according to the steps to be performed.

When the valve 54 of the patient port 53 is open, the patient line tube 58 is in fluid communication with the second compartment 23, when the valve 54 of the patient port 53 is closed, fluid communication between the patient line tube 58 and the second compartment 23 is prevented.

When the first dialysis valve 42 of the first dialysis fluid port 40 is open, the first dialysis fluid line tube 59 is in fluid communication with the first compartment 22, when the first dialysis valve 42 of the first dialysis fluid port 40 is closed, fluid communication between the first dialysis fluid line tube 59 and the first compartment 22 is prevented.

When the second dialysis valve 43 of the second dialysis fluid port 41 is open, the second dialysis fluid line tube 61 is in fluid communication with the first compartment 22, when the second dialysis valve 43 of the second dialysis fluid port 41 is closed, fluid communication between the second dialysis fluid line tube 61 and the first compartment 22 is prevented.

When the heater valve 45 of the heater port 44 is open, the heater line tube 63 is in fluid communication with the first compartment 22, when the heater valve 45 of the heater port 44 is closed, fluid communication between the heater line tube 63 and the first compartment 22 is prevented.

When the drain valve 39 of the drain port 36 is open, the drain fluid line tube 65 is in fluid communication with the first compartment 22, when the drain valve 39 of the drain port 36 is closed, fluid communication between the fluid drain line tube 65 and the first compartment 22 is prevented.

When the by-pass valve 51 of the by-pass port 52 is open, the heater line tube 63 is in fluid communication with the second compartment 23; when the by-pass valve 51 of the by-pass port 52 is closed, fluid communication between the heater line tube 63 and the second compartment 23 is prevented.

As shown in FIGS. 6A and 6B and 7, when the actuator keeps the plunger 15 of the occlusion element 7 in the retracted position of FIG. 6A, the plastic sheet 21 is spaced from the edge of the hollow barrel 38 and fluid may flow between the hollow barrel 38 and the first compartment 22 (valve open).

When the actuator moves the plunger 15 of the occlusion element 7 in the forward position of FIG. 6B and keeps plunger 15 in said forward position, the plunger 15 is accommodated in part in the hollow barrel 38.

The plunger 15 pushes, deforms and keeps a portion of plastic sheet 21 against the edge of the hollow barrel 38. The hollow barrel 38 is a seat for the plunger 15 and for the portion of plastic sheet 21 trapped between. A fluid flow between the hollow barrel 38 and the first compartment 22 is prevented (valve closed). All valves work in this way.

Before patient treatment, the manifold assembly 3 is primed. A possible priming sequence is represented in the following table (Table 1).

TABLE 1

| Step | From | To | Valves Open | Pump Direction |
|---|---|---|---|---|
| 1 | Heater bag | Drain | By-pass valve Drain valve | ClockWise |
| 2 | First supply bag | Expansion chambers | First dialysis valve | CounterClockWise |
| 3 | Expansion chambers | Drain | Drain valve | ClockWise |

TABLE 1-continued

| Step | From | To | Valves Open | Pump Direction |
|------|------|-----|-------------|----------------|
| 4 | Second supply bag | Expansion chambers | Second dialysis valve | CounterClockWise |
| 5 | Expansion chambers | Drain | Drain valve | ClockWise |
| 6 | Heater bag | Patient | Heater valve Patient valve | CounterClockWise |

Another priming procedure may be performed using communication vessels as disclosed in the following Table 2.

TABLE 2

| Step | From | To | Valves Open | Pump Direction |
|------|------|-----|-------------|----------------|
| 1 | Heater bag | Patient line tube | All valves and yielding pump tube open | — |

After priming, patient treatment may be started.

According to an embodiment of the method for controlling the peritoneal dialysis apparatus 1 (FIGS. 8 and 12), the control unit 5 commands the peritoneal dialysis apparatus 1 to move the dialysis fluid from the first supply bag 60 to the patient P.

The control unit 5 closes and keeps closed the heater valve 45, the by-pass valve 51, the second dialysis valve 43 and the drain valve 39, opens and keeps open the first dialysis valve 42 and the patient valve 54. The control unit 5 commands the motor to rotate the peristaltic pump 6 in a first rotation direction (CounterClockWise in FIG. 8) to pump the dialysis fluid from the first compartment 22 to the second compartment 23.

An auxiliary in-line heater, not shown, may be placed on the first dialysis fluid line tube 59 to heat the dialysis fluid while flowing through said dialysis fluid line tube 59 and towards the patient P.

According to another embodiment of the method for controlling the peritoneal dialysis apparatus 1 (FIGS. 9, 10, 11, 13, 14, 15), the control unit 5 commands the peritoneal dialysis apparatus 1 to move the dialysis fluid from the first supply bag 60 towards the heater bag 64. In this embodiment, the auxiliary in-line heater is not used.

The control unit 5 opens and keeps open the by-pass valve 51 and the first dialysis valve 42 while closes and keeps closed the heater valve 45, the second dialysis valve 43, the drain valve 39 and the patient valve 54. The control unit 5 commands the motor to rotate the peristaltic pump 6 in a first rotation direction (CounterClockWise in FIG. 9) to pump the dialysis fluid from the first compartment 22 to the second compartment 23 and then to the heater bag 64 through the by-pass channel 49.

Once the dialysis fluid has been heated in the heater bag 64 coupled to the heater of the cycler 2, the control unit 5 commands the peritoneal dialysis apparatus 1 to move the heated dialysis fluid from the heater bag 64 towards the patient P.

The control unit 5 opens and keeps open the heater valve 45 and the patient valve 54 and closes and keeps closed the by-pass valve 51, the first dialysis valve 42, the second dialysis valve 43 and the drain valve 39. The control unit 5 commands the motor to rotate the peristaltic pump 6 in a first rotation direction (CounterClockWise in FIG. 10) to pump the dialysis fluid from the first compartment 22 to the second compartment 23.

At the end of the patient treatment, the spent dialysis fluid is removed from the patient P. The control unit 5 commands the peritoneal dialysis apparatus 1 to move the spent dialysis fluid from the patient P towards the drain 66.

The control unit 5 opens and keeps the drain valve 39 and the patient valve 54 and closes and keeps closed the heater valve 45, the by-pass valve 51, the first dialysis valve 42, the second dialysis valve 43. The control unit 5 commands the motor to rotate the peristaltic pump 6 in a second rotation direction (ClockWise in FIG. 11) to pump the dialysis fluid from the second compartment 23 to the first compartment 22.

This treatment sequence is represented in the following table (Table 3).

TABLE 3

| Step | From | To | Valves Open | Pump Direction |
|------|------|-----|-------------|----------------|
| 1 | First supply bag | Heater bag | First dialysis valve By-pass valve | CounterClockWise |
| 2 | Heater bag | Patient | Heater valve Patient valve | CounterClockWise |
| 3 | Patient | Drain | Drain valve Patient valve | ClockWise |

Embodiment 2

Figure 16:
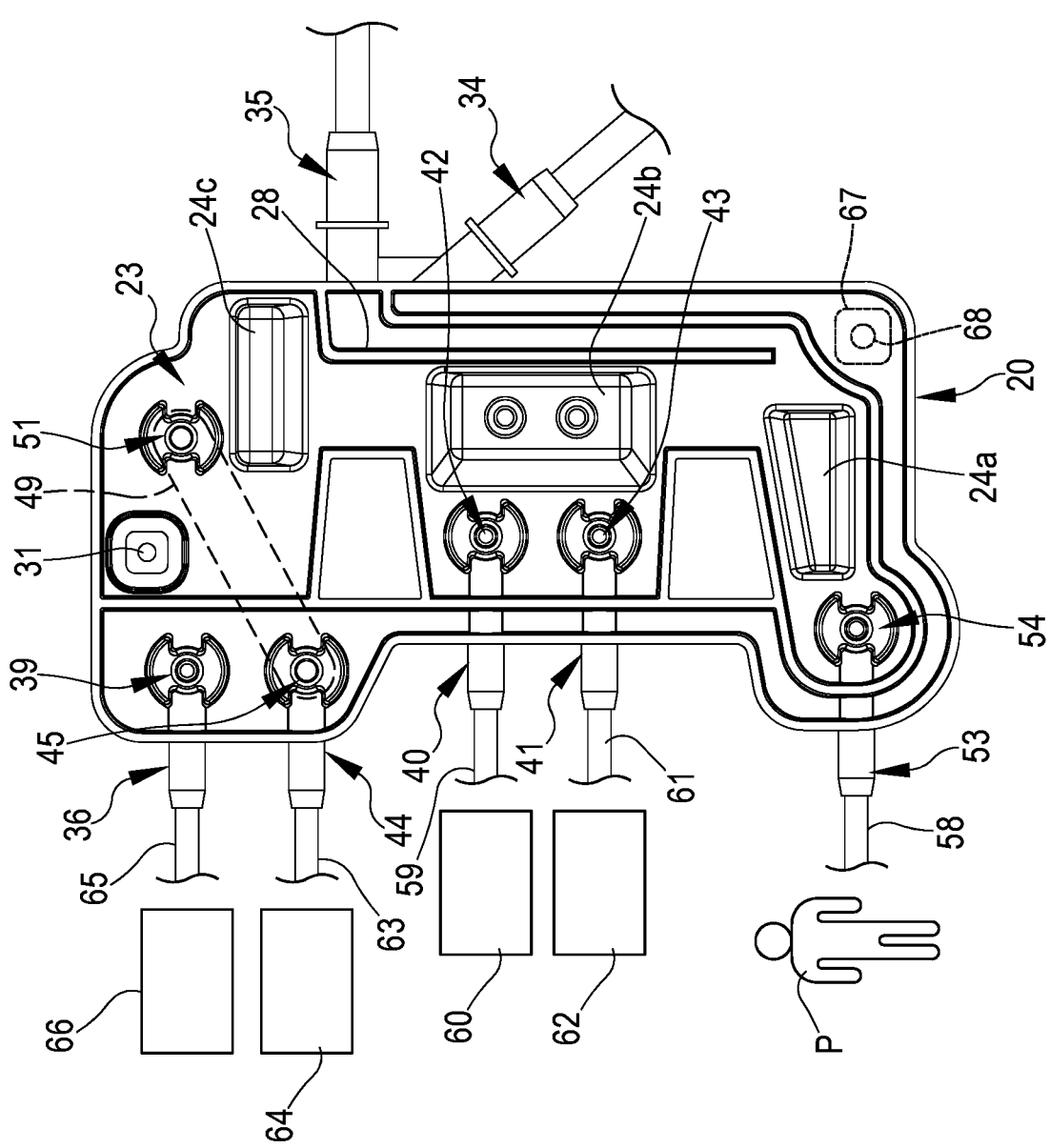
FIG. 16 shows is a rear view of another embodiment of the manifold assembly with some parts removed to illustrate the interior and some other parts schematically represented.
Figure 17:
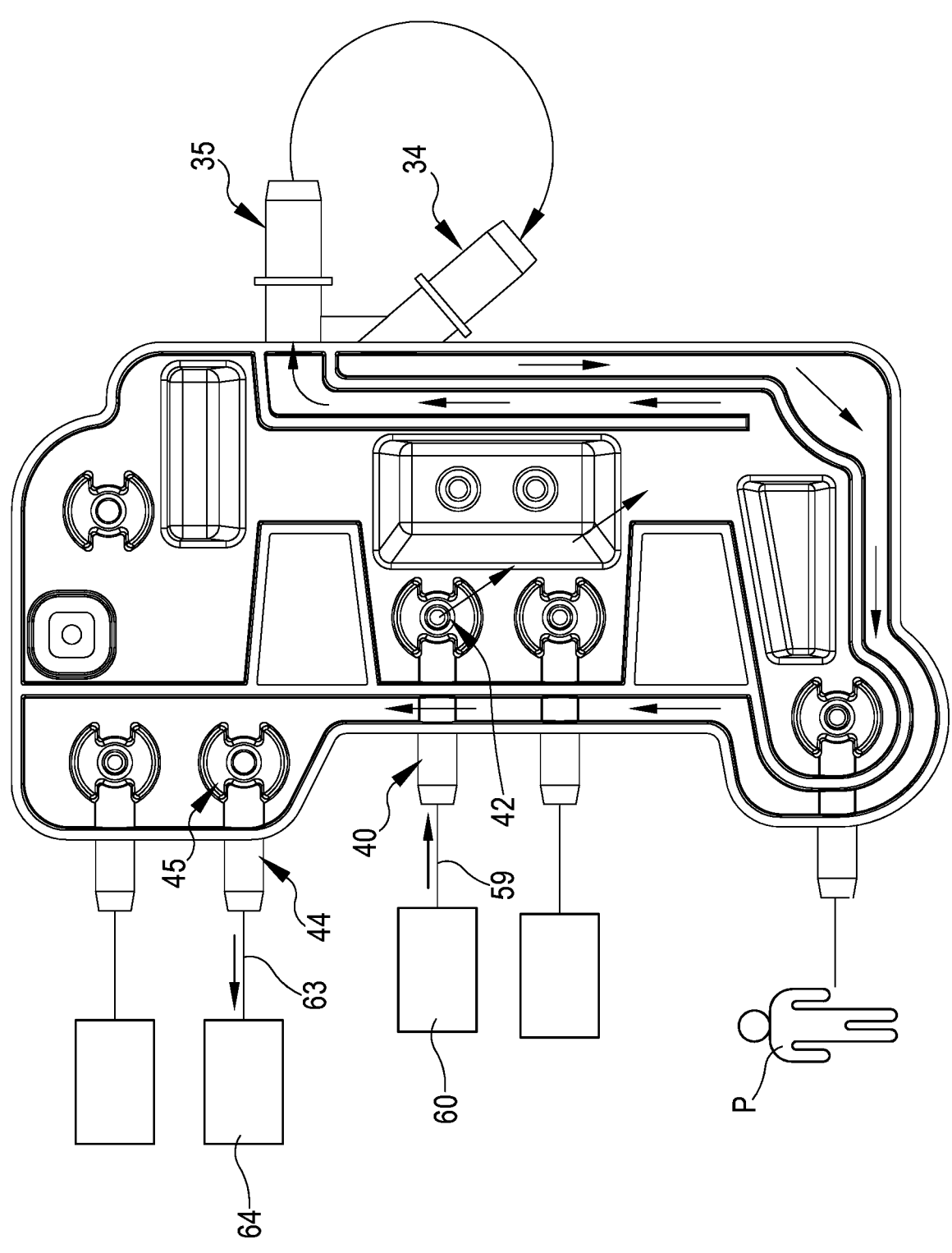
FIG. 17 is the rear view of FIG. 16 illustrating a respective flow configuration.

FIGS. 16 and 17 show another embodiment of the manifold assembly 3 of the peritoneal dialysis apparatus 1 (APD). The cycler 2 of this embodiment is not shown and may have the same structure/architecture disclosed for the first embodiment.

The manifold assembly 3 (FIGS. 16 and 17) that organizes tubing and performs many functions discussed herein is different from the manifold assembly 3 of embodiment 1 in the following features.

As can be seen comparing FIGS. 3 and 16 (the same reference numerals are used for the same elements), the first dialysis port 40 and the second dialysis port 41 open inside the second compartment 23 instead of the first compartment 22. The first dialysis valve 42 and the second dialysis valve 43 are positioned in the second compartment 23 and close to the second expansion chamber 24*b*.

The first dialysis fluid line tube 59 has the first end connected to the first supply bag 60 and the second end connected to the second compartment 23. The second dialysis fluid line tube 61 has the first end connected to the second supply bag 62 and the second end connected to the second compartment 23.

In addition, the drain port 36 and the drain fluid line tube 65 are arranged close to a top of the casing 19 and, when the manifold assembly 3 is properly mounted on the cycler 2, are located above the heater port 44 and the heater line tube 63.

The second inner septum 28 has a first extremity connected to the right long side of the plastic rigid shell 20, close to the second pump port 35 and, differently from the embodiment of FIG. 3, the area of the second compartment 23 with the hole 31 and the breathable membrane 33 is not separated from the by-pass valve 51 by said second inner septum 28.

Furthermore, the hole 31 and the breathable membrane 33 are next to the top short side of the plastic rigid shell 20.

An area 67 of the plastic sheet 21 is configured to be coupled to displacement sensor 68 (shown only schematically) of the cycler 2 when the manifold assembly 3 is properly mounted on the cycler 2.

FIG. 16 shows that said area 67 faces a zone of the first compartment 22 located at a right bottom elbow the substantially U-shaped first elongated passage. The displacement sensor 68 is mounted on the front panel 13 of the cycler 2.

Figure 10:
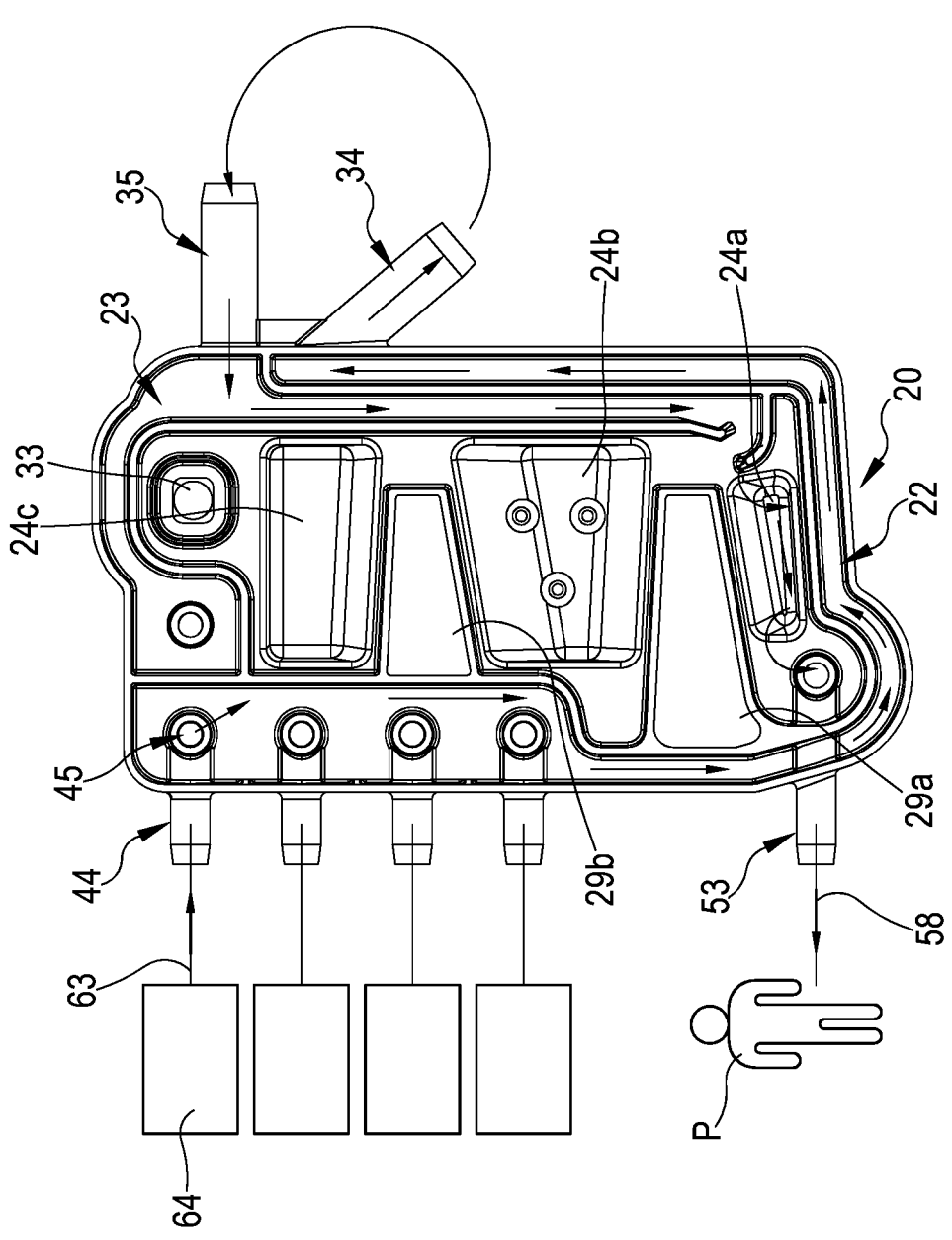
Figure 11:
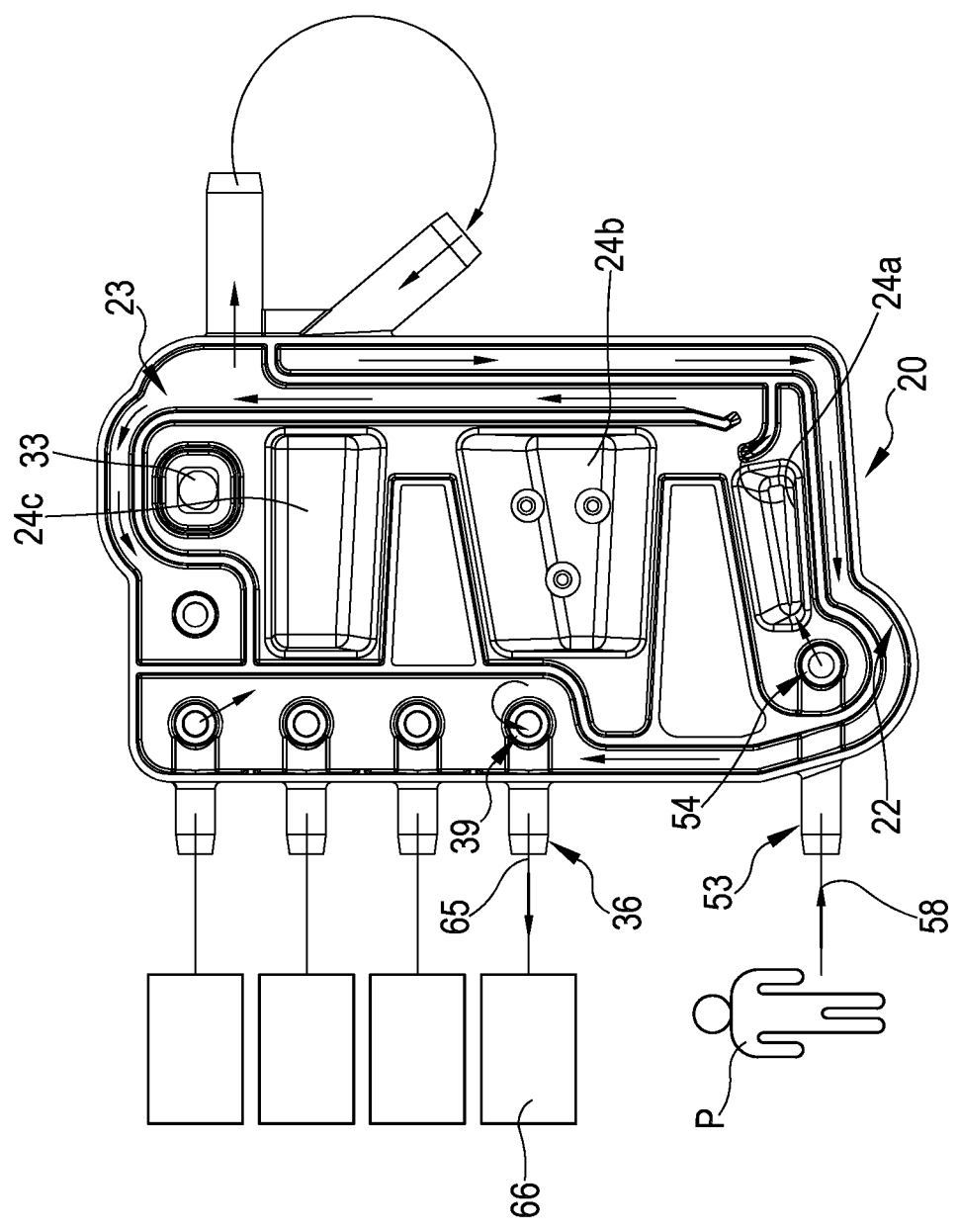

The flow route from the heater bag 64 to the patient P and the flow route from the patient P to drain are the same shown in FIGS. 10 and 11 and disclosed in the previous paragraphs.

Figure 9:
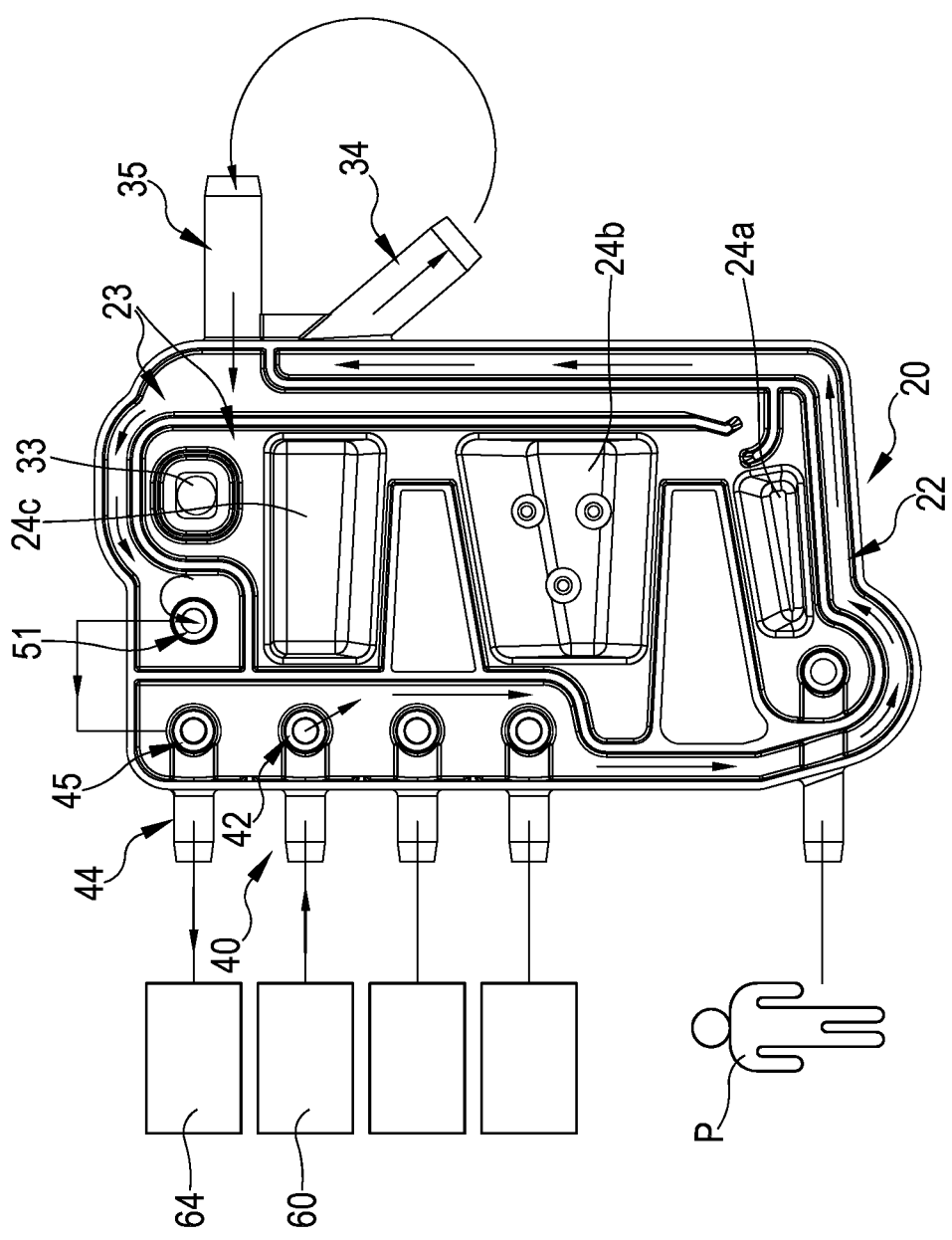

Because of the different position of the first dialysis valve 42 and second dialysis valve 43, the flow route from the first supply bag 60 to the heater bag 64 is other than the one shown in FIG. 9.

Indeed, in this second embodiment (FIGS. 17 and 18), the control unit 5 opens and keeps open the heater valve 45 and the first dialysis valve 42 while closes and keeps closed the by-pass valve 51, the second dialysis valve 43, the drain valve 39 and the patient valve 54. The control unit 5 commands the motor to rotate the peristaltic pump 6 in the second rotation direction (ClockWise in FIG. 9) to pump the dialysis fluid from the second compartment 23 to the first compartment 22.

The treatment sequence for the manifold assembly 3 of the second embodiment is shown in the following table (Table 4).

TABLE 4

| Step | From | To | Valves Open | Pump Direction |
|---|---|---|---|---|
| 1 | First supply bag | Heater bag | Heater valve First dialysis valve | ClockWise |
| 2 | Heater bag | Patient | Heater valve Patient valve | CounterClockWise |
| 3 | Patient | Drain | Drain valve Patient valve | ClockWise |

Before patient treatment, the manifold assembly 3 of the second embodiment is primed. A possible priming sequence is represented in the following table (Table 5).

TABLE 5

| Step | From | To | Valves Open | Pump Direction |
|---|---|---|---|---|
| 1 | Heater bag | Drain | By-pass valve Drain valve | ClockWise |
| 2 | First supply bag | Drain | First dialysis valve Drain valve | ClockWise |
| 3 | Second supply bag | Drain | Second dialysis valve Drain valve | ClockWise |
| 4 | Heater bag | Patient | Heater valve Patient valve | CounterClockWise |

Embodiment 3

Figure 19:
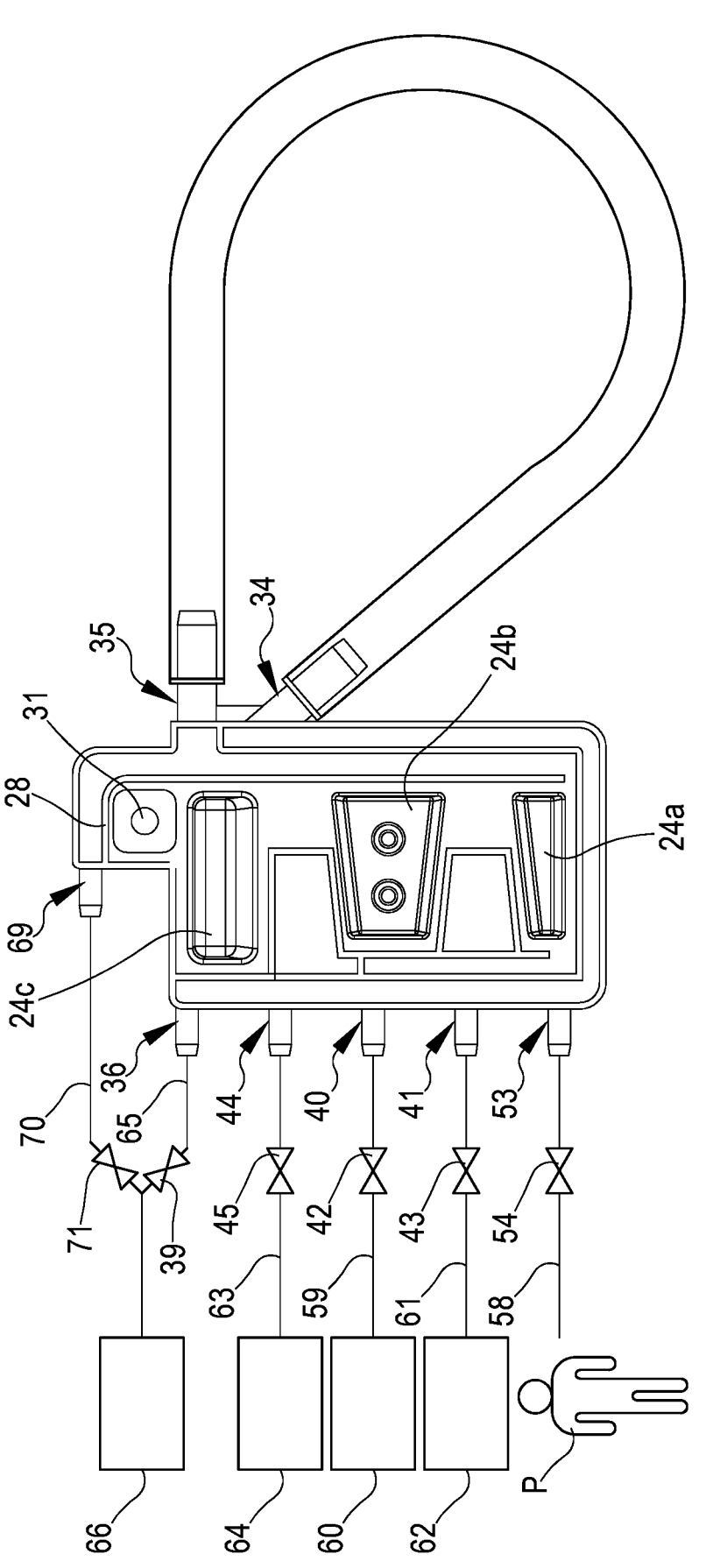
FIG. 19 is a rear view of further embodiment of the manifold assembly with some parts removed to illustrate the interior and some other parts schematically represented.

FIG. 19 shows another embodiment of the manifold assembly 3 of the peritoneal dialysis apparatus 1 (APD). The cycler 2 of this embodiment is different from the first embodiment, because the valves are not part of the casing 7 and the occlusion elements of the cycler 2 are pinch valves.

In this third embodiment, like in the second embodiment, as can be seen comparing FIGS. 3, 16 and 19 (the same reference numerals are used for the same elements), the first dialysis port 40 and the second dialysis port 41 open inside the second compartment 23 instead of the first compartment 22.

All the ports do not comprise valves or part of valves. The drain port 36 and the drain fluid line tube 65 are arranged close to a top of the casing 19, like in the second embodiment.

The second inner septum 28 separates the area of the second compartment 23 with the hole 31 and the breathable membrane from an area of the second compartment 23 with an auxiliary drain port 69 connected to an auxiliary drain fluid line tube 70.

The drain valve 39, first dialysis valve 42, second dialysis valve 43, heater valve 45, patient valve 54 are clamps part of the cycler 2 and operating on tube sections of the drain fluid line tube 65, first dialysis fluid line tube 59, second dialysis fluid line tube 61, heater line tube 63, patient line tube 58. The clamp and the tube section form together a pinch valve.

In addition, an auxiliary drain valve 71 works on the auxiliary drain fluid line tube 70 and the drain fluid line tube 65 merges with the auxiliary drain fluid line tube 70 in a common drain line before reaching the drain 66 (FIG. 19).

The flow route from the heater bag 64 to the patient P and the flow route from the patient P to drain are the same shown in FIGS. 10 and 11 and disclosed in the previous paragraphs (first embodiment).

The flow route from the first supply bag 60 to the heater bag 64 is the same of the second embodiment (see Table 3).

A possible priming sequence is represented in the following table (Table 6).

TABLE 6

| Step | From | To | Valves Open | Pump Direction |
|---|---|---|---|---|
| 1 | Heater bag | Drain | Heater valve Auxiliary drain valve | CounterClockWise |
| 2 | First supply bag | Drain | First dialysis valve Drain valve | ClockWise |
| 3 | Second supply bag | Drain | Second dialysis valve Drain valve | ClockWise |
| 4 | Heater bag | Patient | Heater valve Patient valve | CounterClockWise |

Valves

Figure 20C:
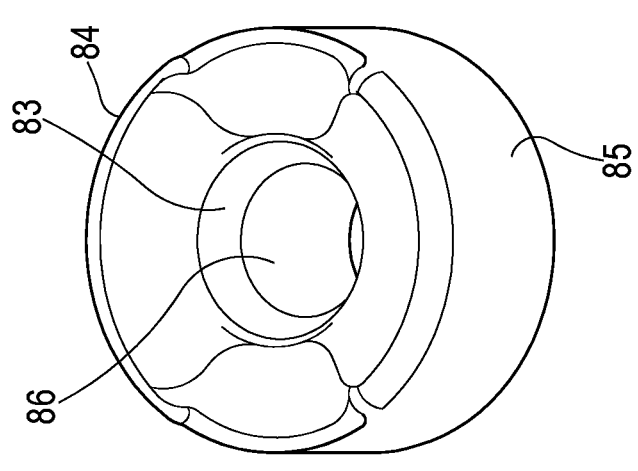
FIGS. 20A, 20B and 20C show embodiments of the valves of the embodiment of FIGS. 16, 17 and 18.
Figure 20B:
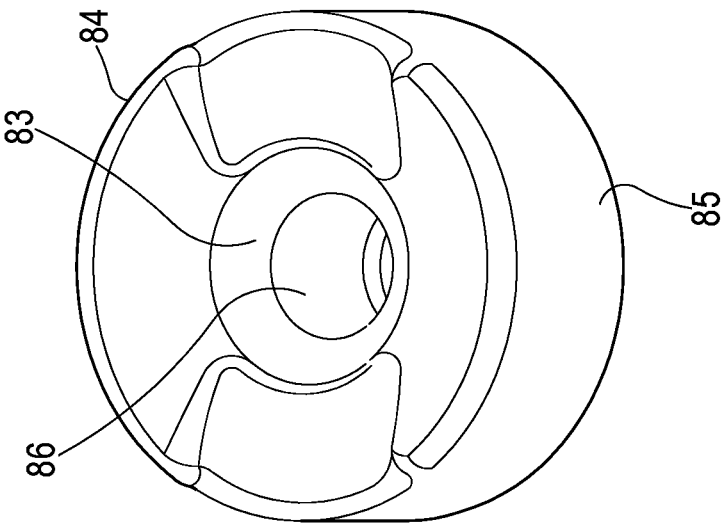
Figure 20A:
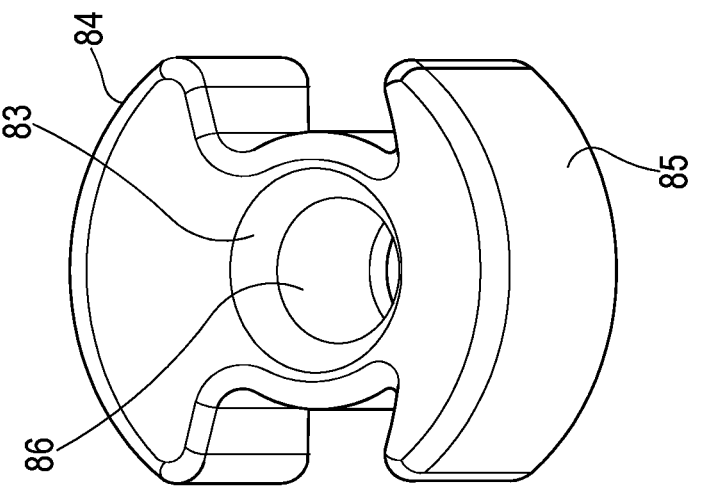

In some embodiments, the valves are part of the casing and are shaped like in FIGS. 20A, 20B, 20C. For instance, all the valves (drain valve 39, first dialysis valve 42, second dialysis valve 43, heater valve 45, by-pass valve 51, patient valve 54) of embodiment two of FIGS. 16 and 17 are of the type shown in FIG. 20A.

This kind of valves is configured to work with the occlusion element 7 illustrated in FIGS. 21A, 21B, 21C, 21D, 22 and 23.

The occlusion element 7 comprises the plunger 15, like the one of FIGS. 6A, 6B and 7, and further comprises a mechanical tensioning plunger 76. Both the plunger 15 and the tensioning plunger 76 are mechanically coupled to an actuator 73, shown in FIGS. 22 and 23.

Figure 22A:
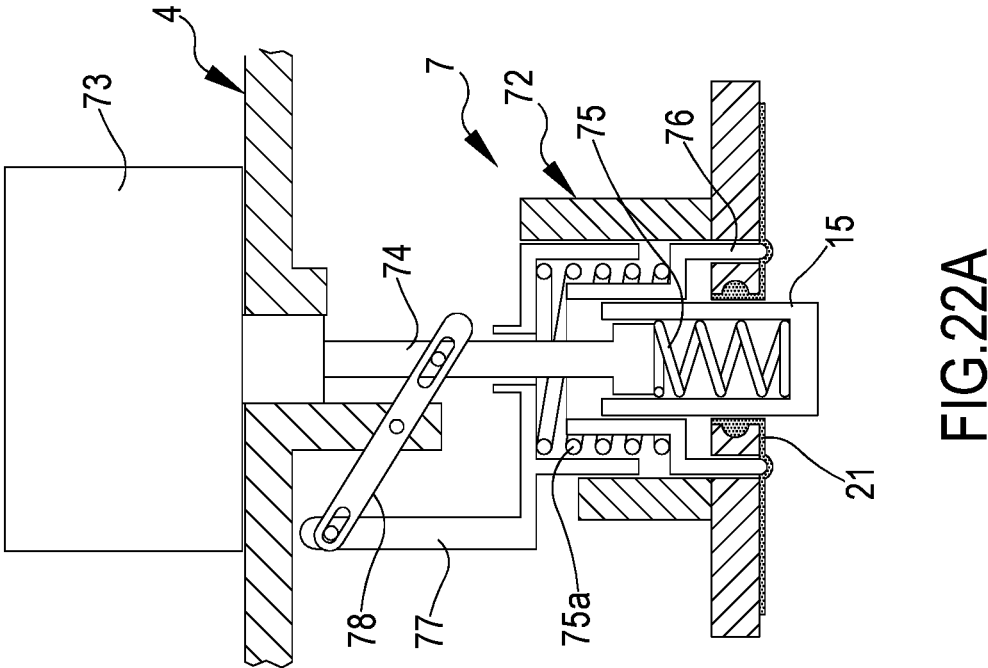
FIG. 22A is a variant of the embodiment of FIG. 22.
Figure 22:
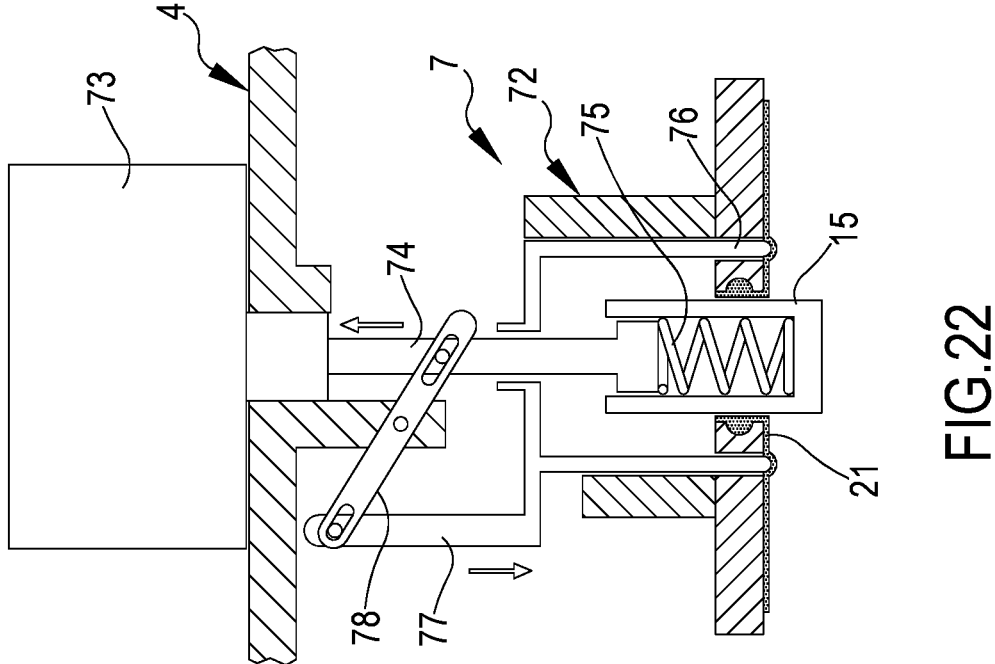
FIG. 22 is an embodiment of the element of FIG. 21A.

In the embodiment of FIG. 22, the actuator 73 is a linear actuator connected to a shaft 74. A distal end of the shaft 74 carries the plunger 15 and a damping and/or resilient element 75 (like a spring) is placed between the distal end and said plunger 15. The plunger 15 is shaped like a cup housing the spring.

The damping and/or resilient element 75 allows to reduce the force exerted on the membrane 21 to avoid damaging said membrane 21.

Like in FIGS. 16 and 17, the actuator 73 is configured to move the plunger 15 along an axial direction and between the retracted position, in which the plunger 15 is spaced from the soft membrane 21 and the port is open, and a forward position, in which the plunger 15 is at least in part accommodated in the seat and the soft membrane 21 is deformed and trapped between said plunger 15 and said seat to close the port.

The membrane tensioner 72 is configured to raise the soft membrane 21 away from the seat when the plunger 15 goes back to the retracted position and to counteract a possible negative pressure tending to keep the valve closed.

The membrane tensioner 72 comprises a tensioning plunger 76 which is also mechanically connected to the actuator 73. The tensioning plunger 76 is shaped substantially like a cylinder, is coaxial to the plunger 15 and surrounds at least in part the plunger 15.

Figure 24:
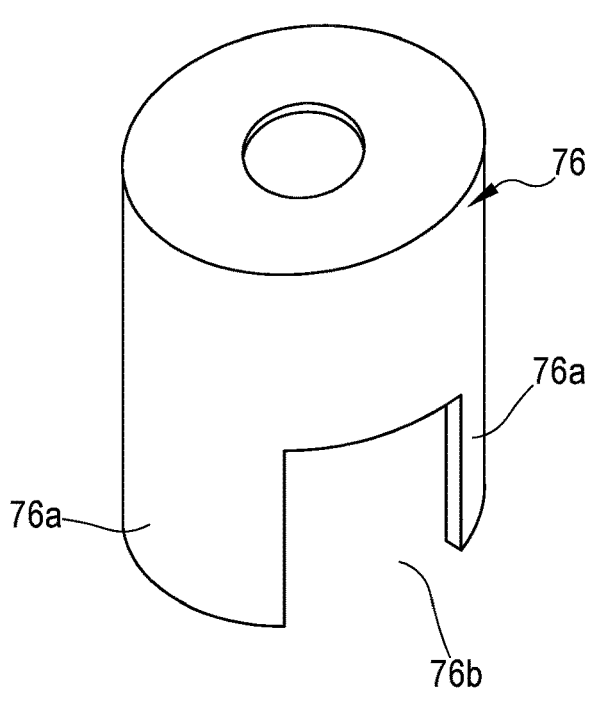
FIG. 24 shows a member of the element of FIG. 22 or 23.

The tensioning plunger 76 comprises two arched walls 76a coaxial to a central axis. The walls 76a are spaced one from the other to delimit two windows 76b between them (FIGS. 24 and 25).

The tensioning plunger 76 is fitted on the shaft 74 and is axially movable along said shaft 74. Borders of the arched walls 76a of the tensioning plunger 76 face the soft membrane 21 and the plunger 15 may protrude from the tensioning plunger 76.

The actuator 73 is also configured to move the tensioning plunger 76 between a retracted position, in which the tensioning plunger 76 is spaced from the soft membrane 21, and a forward position, in which the tensioning plunger 76 engages the soft membrane 21 at locations other than an edge of the seat, to move away the soft membrane 21 from the edge and to stretch said soft membrane 21 above the seat.

In other embodiments, not shown, the tensioning plunger 76 may be moved by an auxiliary actuator, not shown.

The actuator 73 is housed in the box 4 of the cycler 2; the plunger 15, the tensioning plunger 76 and the shaft 74 are guided through openings fashioned in the box 4 of the cycler 2.

Figure 21C:
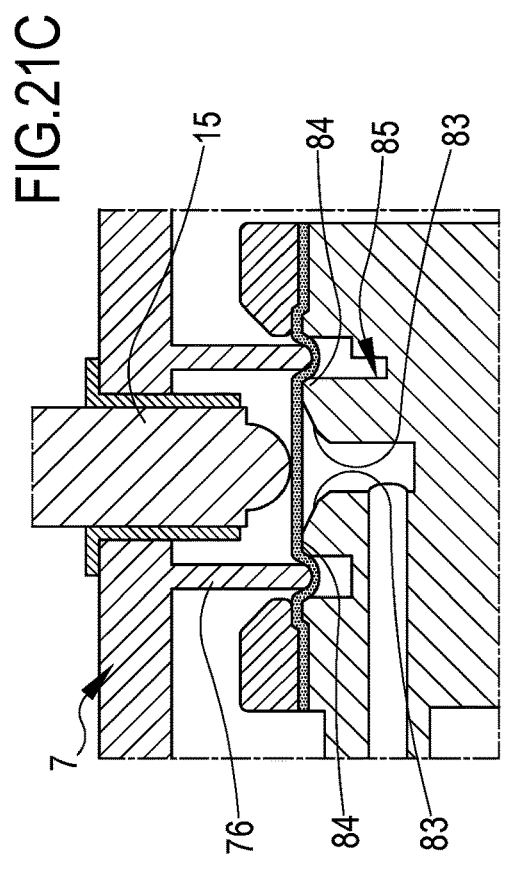
FIGS. 21A to 21D show working steps of the valve of FIG. 20A cooperating with an element of the cycler.
Figure 21D:
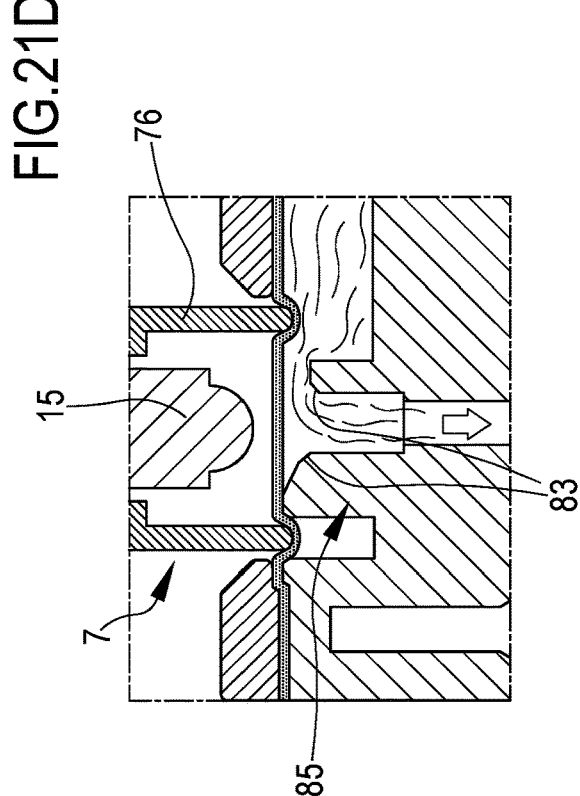
Figure 21A:
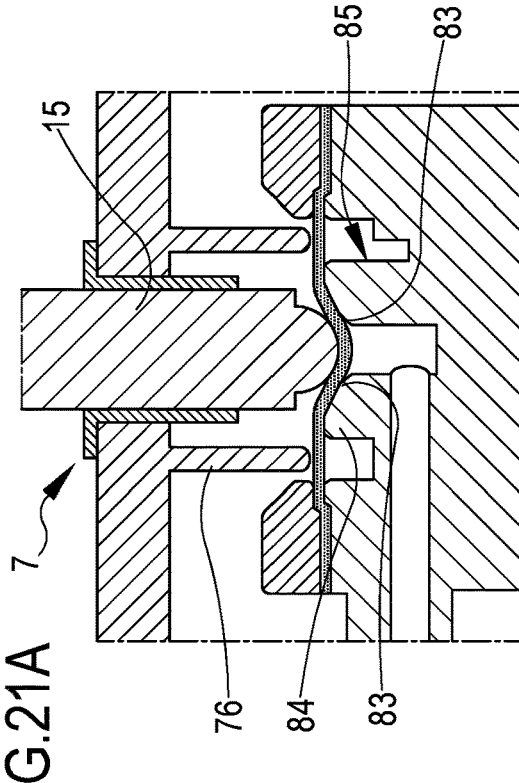
Figure 21B:
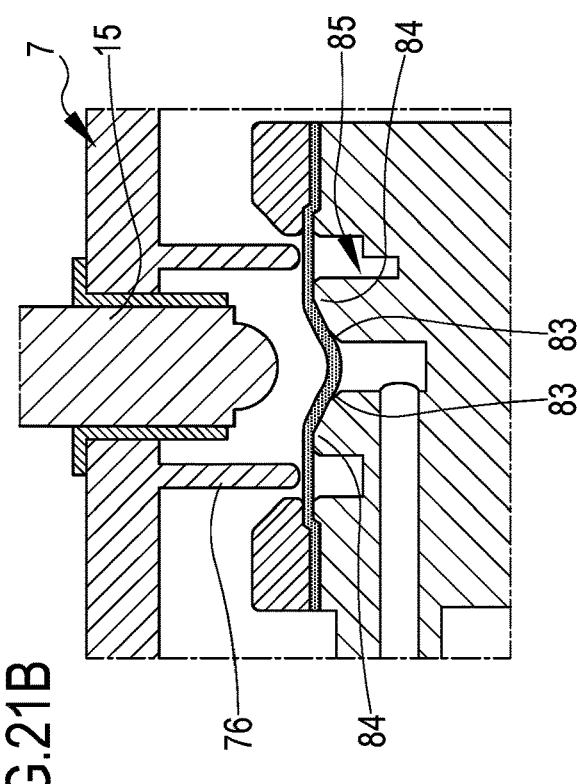

The tensioning plunger 76 is in the retracted position when the plunger 15 is in the forward position (FIGS. 21A and 21B). In this configuration, the plunger 15 protrudes from the tensioning plunger 76.

The tensioning plunger 76 is in the forward position when the plunger 15 is in the retracted position (FIGS. 21C and 21D). In this configuration, the plunger 15 is entirely housed within the tensioning plunger 76 and does not protrude beyond the borders of the tensioning plunger 76.

The occlusion element 7 comprises a reverse mechanism connecting the tensioning plunger 76 and the plunger 15. The reverse mechanism is configured to move the plunger 15 in an opposite direction with respect to a moving direction of the tensioning plunger 76 when the plunger 15 is moved by the actuator 73.

In the embodiment of FIG. 22, the tensioning plunger 76 comprises a projection 77 extending parallel to the shaft 74 and a rocker lever 78. A first end of the rocker lever 78 is hinged to the shaft 74 of the plunger 15, a second end of the rocker lever 78 is hinged to the projection 77 of the tensioning plunger 76 and a middle portion of the rocker lever 78 is hinged to a stationary part of the cycler 2, for instance to a part of the box 4.

When the linear actuator moves the plunger 15 towards the forward position, the rocker lever 78 tilts and moves the tensioning plunger 76 towards the retracted position. When the linear actuator moves the plunger 15 towards the retracted position, the rocker lever 78 tilts and moves the tensioning plunger 76 towards the forward position.

The variant embodiment of FIG. 22A comprises an additional damping and/or resilient element 75a (a spring) coupled to the tensioning plunger 76. In this embodiment, the cylinder defining the tensioning plunger 76 is in two parts. A first part is rigidly connected to the projection 77. A second part carries the borders of the arched walls 76a of the tensioning plunger 76 facing the membrane 21. The additional damping and/or resilient element 75a is interposed between the first and the second part.

The additional damping and/or resilient element 75a allows to reduce the force exerted on the membrane 21 by the tensioning plunger 76, to avoid damaging said membrane 21. A further function of the additional damping and/or resilient element 75a is to compensate for possible plastic deformation of the membrane 21 that may lose elasticity and may plastically deform over time. Even if the membrane 21 is plastically stretched, the additional damping and/or resilient element 75a is always able to push the borders of the arched walls 76a of the tensioning plunger 76 against the membrane 21 (forward position), to move away said soft membrane 21 from the edge and to stretch said soft membrane 21 above the seat.

Figure 23:
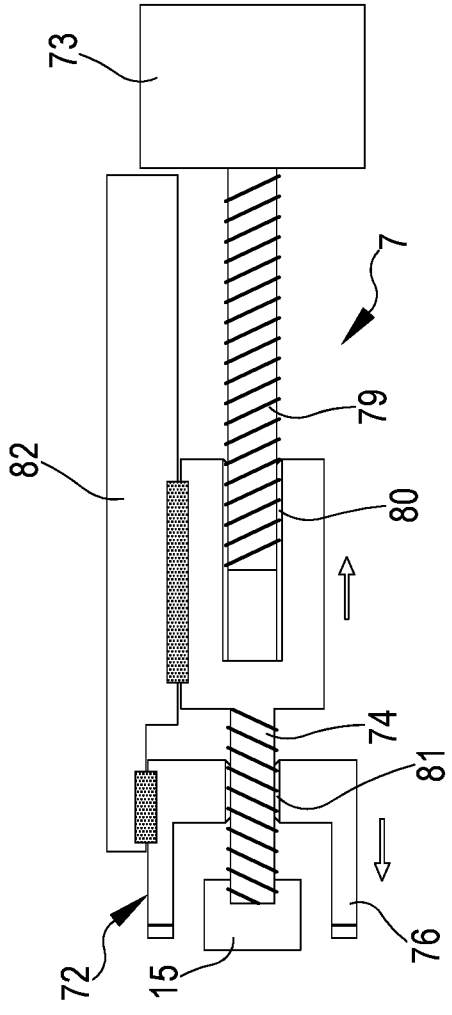
FIG. 23 shows another embodiment of the element of FIG. 21A.

In the embodiment of FIG. 23, the actuator 73 is a stepper motor comprising a rotatable shaft 79 connected to the shaft 74 of the plunger 15. The rotatable shaft 79 has an outer thread and is coupled, through a left hand threaded coupling 80, to an inner thread of the shaft 74.

The shaft 74 has an outer thread and is coupled, through a right hand threaded coupling 81, to an inner thread of the tensioning plunger 76.

The tensioning plunger 76 and the shaft 74 are axially guided by a stationary element 82, for instance to a part of the box 4.

The rotation of the rotatable shaft 79 caused by the stepper motor makes the shaft 74 moving only axially in a first direction (the shaft 74 does not revolve), e.g. towards the forward position of the plunger 15.

Because of the left hand threaded coupling 80, the axial movement of the shaft 74 drives the rotation of the tensioning plunger 76 and, due to a different pitch of the left hand threaded coupling 80 and right hand threaded coupling 81, also the axial movement of said tensioning plunger 76 in a second direction, opposite the first direction, e.g. towards a retracted position of the tensioning plunger 76.

When the stepper motor moves the plunger 15 towards the forward position, the left hand threaded coupling 80 and right hand threaded coupling 81 work to move the tensioning plunger 76 towards the retracted position. When the stepper motor moves the plunger 15 towards the retracted position, the left hand threaded coupling 80 and right hand threaded coupling 81 work to move the tensioning plunger 76 towards the forward position.

In order to properly work with the plunger 15 and with the membrane tensioner 72, the valve has a circular edge 83 delimiting the seat and also an auxiliary edge 84 extending in part around the circular edge 83 and spaced with respect to said edge 83.

Instead of the hollow barrel 38 of FIGS. 6A, 6B and 7, the valve comprises a shaped member 85 which protrudes from the bottom surface of the respective compartment 22, 23 and comprises the edge 83 and the auxiliary edge 84.

The shaped member 85 is substantially cylindrical and delimits a central cylindrical cavity 86. The edge 83 delimits an upper part of said cavity 86 and the auxiliary edge 84 comprises two arch shaped parts coaxial to the cavity and to the edge 83.

As shown in FIGS. 20A to 21D, the auxiliary edge 84 is raised with respect to the edge 83 such that, when the manifold assembly 3 is properly mounted on the site 14 of the cycler 2, the auxiliary edge 84 is closer to the occlusion element than the edge 83.

FIGS. 21A to 21D show working steps of the assembly comprising the valve and the occlusion element 7.

In FIG. 21A, the valve is closed. The plunger 15 is in the forward position and in part accommodated in the seat, the soft membrane 21 is trapped between said plunger 15 and the edge 83.

In FIG. 21B, the valve is still closed even if the plunger 15 is partly raised, because of negative pressure which keeps the soft membrane 21 against the edge 83.

In FIG. 21C, the valve is open, because the tensioning plunger 76 in the forward position partly surrounds the shaped member 85 and the auxiliary edge 84 and pulls the soft membrane 21 against the auxiliary edge 84. This way, the soft membrane 21 is detached from the edge 83.

In this position, the shaped member 85 is at least in part positioned inside the tensioning plunger 76. Each arched wall 76a of the tensioning plunger 76 is placed close to one of the two arch shaped part of the auxiliary edge 84 and radially outside said arch shaped part of the auxiliary edge 84, as shown in FIG. 25.

The windows 76b face radial openings delimited between the arched walls 76a and allow fluid communication between the cylindrical cavity 86 and the first or second compartment 22, 23, therefore the valve is open (FIG. 21D).

The structure of valve and occlusion element 7 just disclosed may be also part of other kind of medical apparatuses (e.g. dialysis apparatuses for extracorporeal treatment of blood), not necessarily of the peritoneal dialysis apparatus disclosed above.

The medical apparatus may comprise a dialysis machine and a manifold assembly and the manifold assembly is mounted or mountable on the dialysis machine.

The manifold assembly comprises a casing comprising a rigid shell and at least one soft membrane, the rigid shell and soft membrane delimit at least a first fluid passage. The rigid shell comprises at least one port in fluid communication with the first fluid passage and with a second fluid passage. The at least one port has a seat and the soft membrane facing the seat.

The dialysis machine comprises at least one occlusion element 7 which, when the manifold assembly is properly mounted on the dialysis device, faces the seat with the soft membrane 21 there between. The seat is configured for accommodating, at least partially, a respective occlusion element 7 of the dialysis machine.

The dialysis apparatus may be an apparatus for extracorporeal treatment of blood comprising: a blood treatment device; an extracorporeal blood circuit coupled to the blood treatment device; a blood pump, wherein a pump section of the extracorporeal blood circuit being configured to be coupled to the blood pump; a treatment fluid circuit operatively connected to the extracorporeal blood circuit and/or to the blood treatment device. The treatment fluid circuit comprises a dialysis line connected to a fluid chamber of the treatment unit and a fluid evacuation line connected to the fluid chamber. The treatment fluid circuit comprises an infusion circuit comprising one or more infusion lines of a replacement fluid. The manifold assembly may be part of the extracorporeal blood circuit or of the treatment fluid circuit.

Calibration

The manifold assembly 3 described above may be used to calibrate the peristaltic pump 6, i.e. to estimate the stroke liquid volume of the yielding pump tube 55 connected to the peristaltic pump 6 in order to reach volumetric accuracy measure requirements.

The following description is referred to the manifold assembly 3 of the second embodiment of FIGS. 16 and 17. This embodiment is illustrated also in FIGS. 25 and 26. The upper part of the second compartment 23 and the air buffer volume are in fluid communication, through the hole 31, the breathable membrane 33 and an air filter 88, with an auxiliary chamber 87 part of the cycler 2. The pressure transducer 10 is connected to the auxiliary chamber 87 and an air valve 89 allows to open or close communication of the auxiliary chamber 87 with ambient air.

The peristaltic pump 6 comprises an encoder or is coupled to an encoder, not shown in the attached Figures. The encoder is operatively connected to the control unit 5 and is configured to detect the position and movement of the pressing rollers 6a of the peristaltic pump 6.

The control unit 5 is operatively connected to the motor of the peristaltic pump 6, to the first level sensor 8, to the second level sensor 9, to the air valve 10, to the actuators of the occlusion elements 7 and to the pressure transducer 10 and is configured and/or programmed to calibrate the peristaltic pump 6 according to the method here detailed.

Figure 26:
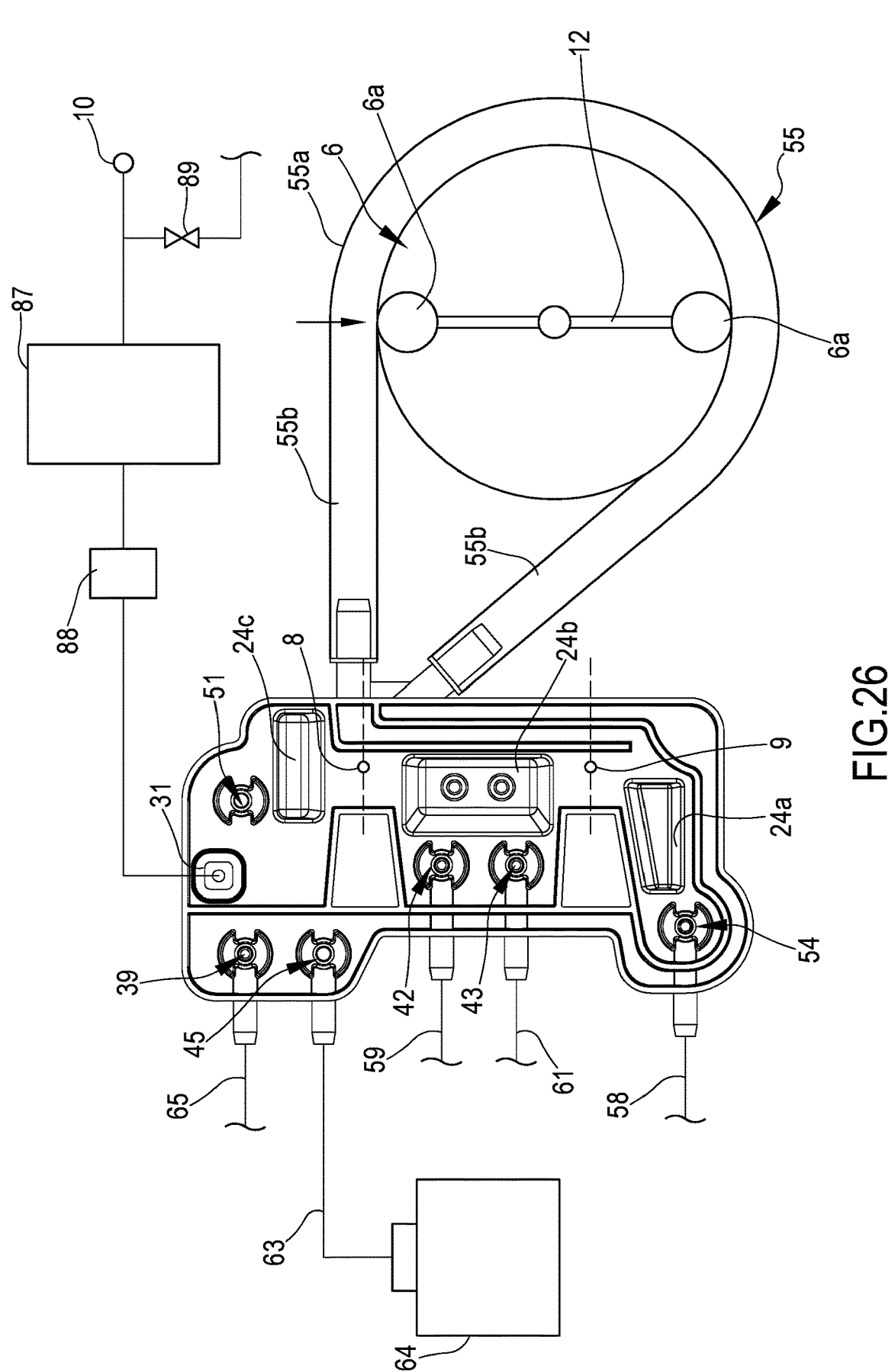
FIG. 26 shows the manifold assembly of FIGS. 16 and 17 configured to perform a method of calibration.

As shown in FIG. 26, the first level sensor 8 or high level sensor and the second level sensor 9 or low level sensor, delimit a high level "C" and a low level "A" in the second compartment 23.

A first volume "V1" is delimited in the second compartment 23 below the low level "A". The first volume "V1" is about 10 ml. A second volume "V2" is delimited in the second compartment 23 between the low level "A" and the high level "C". The second volume "V2" is between two and four times a nominal stroke liquid volume of the peristaltic pump 6. The nominal stroke liquid volume of the peristaltic pump 6 may be 7 ml and the second volume "V2" is about 21 ml. A third volume "V3" is delimited in the second compartment 23 above the high level "C". The third volume "V3" is about 15 ml. The auxiliary chamber 87 delimits inside a fourth volume "V4" of a about 26 ml. A sum of the second, third and fourth volume is about 62 ml.

The yielding pump tube 55 shaped as a loop comprises a rounded part 55a and two straight parts 55b. The rounded part 55a and two straight parts 55b form a single tube. The straight parts 55b are respectively connected to the first pump port 34 and the second pump port 35. The rounded part 55a is configured to be pressed and deformed/squeezed by the pressing rollers 6a of the peristaltic pump 6.

Looking at FIG. 25, if the peristaltic pump 6 rotates counterclockwise, each of the two pressing rollers 6a starts squeezing the rounded part 55a at a bottom portion, between the rounded part 55a and the lower of the two straight parts 55b, and releases the rounded part 55a at a top portion, between the rounded part 55a and the upper of the two straight parts 55b.

In order to calibrate the peristaltic pump 6, i.e. to estimate the stroke liquid volume of the yielding pump tube 55, the following procedure is performed (reference is made to FIGS. 25 to 28).

The drain valve 39, first dialysis valve 42, second dialysis valve 43, by-pass valve 51, patient valve 54 are closed. The heater valve 45 is open and the heater bag 64 is filled with water. The air valve 89 is open.

The control unit 5 controls the peristaltic pump 6 to start rotating counterclockwise, to pump water from the heater bag 64 into the first compartment 22 and then into the second compartment 23. When the low level sensor 9 detects water ($A^{II}$ in FIG. 27), the peristaltic pump 6 is stopped.

Figure 27:
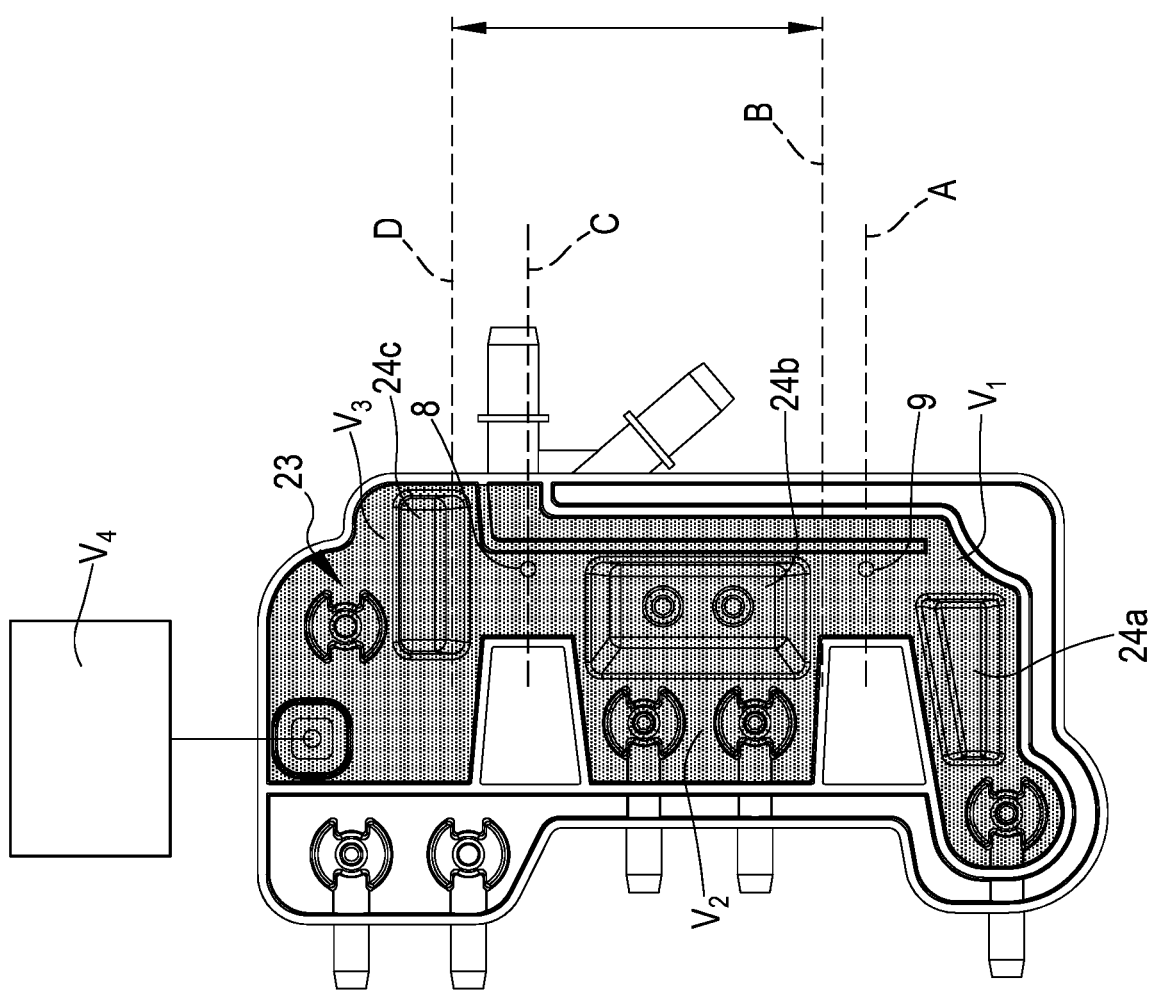
FIG. 27 shows the manifold assembly of FIG. 26 and liquid levels in the manifold during calibration.
Figure 28:
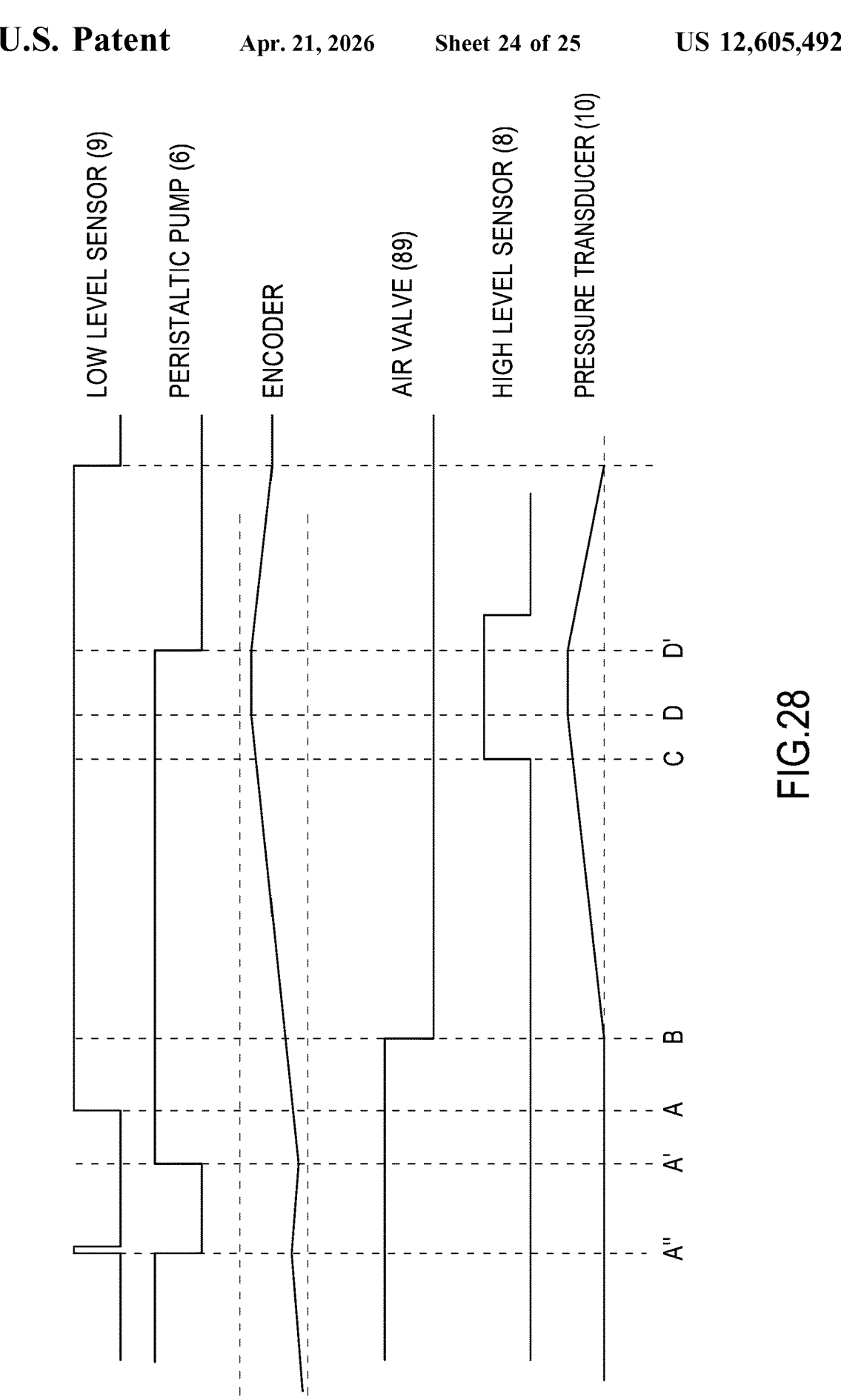
FIG. 28 is a chart showing the method of calibration.
Figure 29:
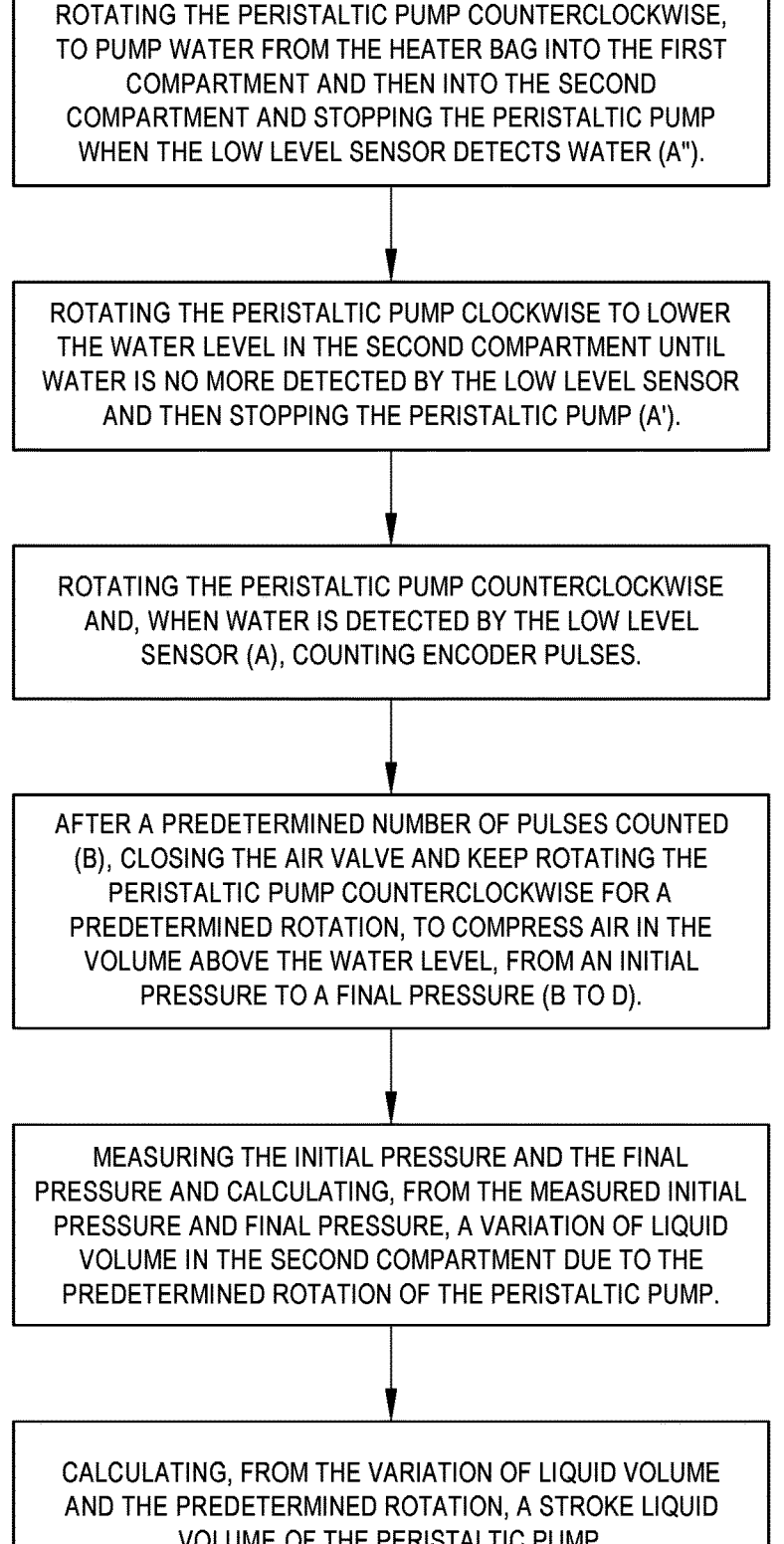
FIG. 29 is a flowchart showing the method of calibration.

The peristaltic pump 6 is then rotated clockwise to lower the water level until water is no more detected by the low level sensor 9 and then stopped again ($A^{I}$ in FIG. 27).

The peristaltic pump 6 is again rotated counterclockwise. When the low level sensor 9 detects again water (low liquid level A in FIGS. 26 and 27), the control unit 5 controls the peristaltic pump 6 to keep rotating counterclockwise and pumping water in the second compartment 23. Meanwhile, the control unit 5 starts counting encoder pulses starting from the detection of water by the low level sensor 9.

When a predetermined number of pulses "Delta_Encoder_Pulses" (e.g. 280 pulses), corresponding to a predetermined angle of rotation "Delta" (e.g. 105°) of the peristaltic pump 6, is reached and the water level is at a first level B (FIGS. 26 and 27), the air valve 89 is closed and the peristaltic pump 6 to keeps on rotating counterclockwise to pump more water in the second compartment 23 and to compress air in the volume above the water level.

The position of one of the two pressing rollers 6a at the end of the predetermined angle "Delta" of rotation is a predetermined position. Such predetermined position may be at a portion of the yielding pump tube 55 between the rounded part 55a and one of the two straight parts 55b. The water level when the pressing roller 6a is in the predetermined position is the first level B. An extra volume "Extra_Volume" of water is pumped to raise the level from the low liquid level A to the first level B (FIGS. 26 and 27).

Starting from said predetermined position of the peristaltic pump 6 and from the first level B, the control unit 5 rotates the peristaltic pump 6 of a counterclockwise predetermined rotation "Rotor_rev" defined by "n" half-revolutions of the peristaltic pump 6, where "n" is an integer (e.g. n=7). The rotational speed of the peristaltic pump 6 may be 5 rpm.

This way, at the end of the "n" half-revolutions, the same pressing roller 6a is positioned again in the predetermined position and the water level is raised to a second level D.

Since the pressing roller 6a passes in the predetermined position several times during the "n" half-revolutions, the water level is sensed through the high level sensor 8 and the rotation of the peristaltic pump 6 is stopped when the pressing element 6a is in the predetermined position for a first time after sensing the high level C (FIGS. 26 and 27).

Air pressure in the second compartment 23 is measured by the pressure transducer 10. An initial pressure $P_{Init}$ before air compression (first level B) and a final pressure $P_{Final}$ after air compression (second level D) are taken. The initial pressure $P_{Init}$ is about 0 mmHg (differential pressure with respect to atmospheric pressure) and the final pressure is about 400 mmHg.

After stopping the rotation of the peristaltic pump 6 and before taking the final pressure $P_{Final}$, it is provided for waiting for a stabilizing time and keeping on measuring pressure (DI in FIG. 27), to check for possible leakages.

A variation of liquid volume "Vol_Moved" in the second compartment 23, due to the rotation of the peristaltic pump 6 of the predetermined rotation "Rotor_rev", is then calculated as a function of an initial air volume "Compensated_Volume" above the first level B and of the initial pressure $P_{Init}$ and the final pressure $P_{Final}$.

The initial air volume "Compensated_Volume" is a difference between a volume of air above the low liquid level "A" (i.e. V2+V3+V4) and the extra volume of water "Extra_Volume", wherein the extra volume of water "Extra_Volume" is the volume of water between the first level B and the low liquid level A, i.e. the volume of water moved by the rotation "Delta" of the peristaltic pump 6.

The stroke liquid volume "Stroke_Vol_Press" of the peristaltic pump 6 is calculated as a ratio between the variation of liquid volume "Vol_Moved" and the "n" half-revolutions of the peristaltic pump 6. The calculation of the stroke liquid volume "Stroke_Vol_Press" as disclosed may be executed consecutively two to five times and an average stroke liquid volume is determined.

The method of calibration may also be implemented in other medical apparatuses comprising a medical machine provided with a peristaltic pump and comprising a manifold assembly, for instance in an apparatus for extracorporeal treatment of blood of the kind above disclosed.

The procedure detailed above may be summarized through the following formulas.

a. Vol_Extra=2*(Delta_Encoder_Pulses/m)*Stroke_Vol_Press b. Compensated_Volume=((V2+V3+V4)−Vol_Extra)

c. Vol_Moved=Compensated_Volume*((Pressure_Final−Pressure_Init)/Pressure_Final)

d. Rotor_rev=(Zc−Yc)/m e. Stroke_Vol_Press=2*(Vol_Moved/Rotor_rev f. Stroke_Vol_Press=2*(m/(Zc−Yc))*((V2+V3+V4)−(Delta_Encoder_Pulses/2m*Stroke_Vol_Press))*((Pressure_Final−Pressure_Init)/Pressure_Final))

Stroke_Vol_Press may be calculated from equation f., wherein:

| | |
|---|---|
| Stroke_Vol_Press | Ratio between the variation of liquid volume "Vol_Moved" (B to D in FIG. 26) and the "n" half-revolutions of the peristaltic pump 6 between the predetermined positions before the air compression (first level B) and after air compression (second level D). |
| m | Number of pulses (e.g. 480 pulses) measured by the encoder per each revolution of the peristaltic pump 6. |
| Zc – Yc | Number of pulses measured by the encoder (B to D in FIG. 26) during the "n" half-revolutions of the peristaltic pump 6. |
| V2 + V3 + V4 | Volume of air above the low liquid level A. |
| Delta_Encoder_Pulses | Number of pulses measured by the encoder (e.g. 280 pulses) when liquid level is raised from A to B. |
| Pressure_Final | Final pressure after compression (C and D). |
| Pressure_Init | Initial pressure before compression (B). |

The invention claimed is:

1. A manifold assembly for a peritoneal dialysis apparatus, the manifold assembly comprising:

a casing delimiting internally a first compartment and a second compartment;

a yielding pump tube having a first end fluidly coupled to the first compartment and a second end fluidly coupled to the second compartment, wherein the yielding pump tube extends outside the casing to be coupled to a peristaltic pump of a cycler of the peritoneal dialysis apparatus, wherein the casing comprises a first pump port connected to the first end of the yielding pump tube and a second pump port connected to the second end of the yielding pump tube; and

a plurality of line tubes each having a first end connected to the first compartment or to the second compartment and a second end connected to a fluid source, a drain, or a patient, wherein the casing comprises a plurality of ports each connected to the first end of one line tube of the plurality of line tubes, wherein the casing has a flattened shape provided with a front, a back, and a plurality of sides, wherein the back is configured to be coupled to a front panel of the cycler, and wherein the first pump port and the second pump port are placed on a first side of the casing, wherein the plurality of ports are placed on a second side of the casing, opposite the first side.

2. The assembly of claim 1, wherein each of the first pump port, the second pump port, and the plurality of ports protrudes from the respective side of the casing.

3. The assembly of claim 1, wherein each of the first pump port, the second pump port, and the plurality of ports is shaped like a hollow cylinder.

4. The assembly of claim 3, wherein the hollow cylinders of the plurality of ports are parallel to each other.

5. The assembly of claim 3, wherein the hollow cylinders of the first pump port and the second pump port diverge from each other away from the casing such that the yielding pump tube is shaped as a loop having an omega shape.

6. The assembly of claim 1, wherein the casing has an outline with two long sides and two short sides, wherein the first side and the second side are sides of the casing that are longer than a third side and a fourth side.

7. The assembly of claim 1, wherein the casing comprises a rigid shell, defining the front and the plurality of sides of the casing, and one soft membrane defining the back of the casing.

8. The assembly of claim 1, wherein the casing has through apertures passing through the casing, wherein the through apertures are configured to engage with retaining elements of the cycler.

9. The assembly of claim 1, wherein the casing comprises at least one protrusion delimiting at least one expansion chamber in the second compartment, such that the at least one expansion chamber has a depth greater than a depth of a remaining part of the second compartment, wherein the at least one protrusion protrudes from the front of the casing.

10. The assembly of claim 9, wherein an inner volume of the second compartment, comprising the at least one expansion chamber, is greater than an inner volume of the first compartment, and wherein, when the manifold assembly is mounted on the cycler, an upper part of the second compartment delimits an air buffer volume.

11. The assembly of claim 9, wherein the plurality of expansion chambers are configured to attenuate pressure pulsations from the peristaltic pump, wherein the plurality of expansion chambers are in part delimited in the second compartment by one soft membrane.

12. The assembly of claim 1, wherein the first compartment is a first elongated passage extending between one of the plurality of line tubes and the first end of the yielding pump tube, wherein the first elongated passage is U-shaped.

13. The assembly of claim 9, wherein the casing comprises through apertures passing through the casing, the through apertures being located between two of the plurality of protrusions.

14. The assembly of claim 1, wherein the casing comprises a breathable membrane joined to an edge of a hole in the casing and configured, when the manifold assembly is mounted on the cycler, to put into communication a pressure transducer and/or an air pump of the cycler with an upper part of the second compartment.

15. The assembly of claim 14, wherein the hole in the casing is fashioned in the front of the casing wherein a rigid frame supports the breathable membrane.

16. The assembly of claim 1, wherein the first compartment is a U-shaped elongated passage and the second compartment is partly surrounded by the U-shaped elongated passage.

17. The assembly of claim 1, wherein the plurality of line tubes comprises:

a patient line tube having a first end fluidly coupled to the second compartment and a second end connectable to a peritoneal cavity of the patient, wherein a patient port of the plurality of ports is connected to the first end of the patient line tube; and at least one fluid line tube having a first end fluidly coupled to the first compartment and a second end fluidly coupled to the fluid source or the drain, wherein one line tube of the plurality of line tubes has a first end fluidly coupled to the second compartment and a second end fluidly coupled to the fluid source, wherein fluid ports of the plurality of ports are connected to one of the first ends of the plurality of line tubes.

18. The assembly of claim 1, wherein the casing comprises a by-pass channel in fluid communication with the first compartment, the second compartment, and a heater line tube, wherein the by-pass channel is in part delimited by a cover joined to an exterior surface of the casing.

19. The assembly of claim 18, wherein the first compartment comprises a by-pass port in fluid communication with the by-pass channel, wherein the by-pass port comprises a respective valve or part of a valve, and wherein the by-pass port has a seat for accommodating, at least partially, a respective occlusion element of the cycler.

20. A manifold assembly for a peritoneal dialysis apparatus, the manifold assembly comprising:

a casing delimiting internally a first compartment and a second compartment, wherein the casing has a flattened shape provided with a front, a back, and a plurality of sides, the back being configured for coupling to a front panel of a cycler of the peritoneal dialysis apparatus;

a yielding pump tube having a first end fluidly coupled to the first compartment and a second end fluidly coupled to the second compartment, wherein the yielding pump tube extends outside the casing to be coupled to a peristaltic pump of the cycler, wherein the casing comprises a first pump port connected to the first end of the yielding pump tube and a second pump port connected to the second end of the yielding pump tube; and a plurality of line tubes each having a first end connected to the first compartment or the second compartment and a second end connected to a fluid source, a drain, or a patient, wherein the casing comprises a plurality of ports each connected to the first end of one line tube of the plurality of line tubes, the plurality of line tubes comprising:

a patient line tube having a first end fluidly coupled to the second compartment and a second end connectable to a peritoneal cavity of the patient, at least one fluid line tube having a first end fluidly coupled to the first compartment and a second end connectable to the fluid source or the drain, and at least one additional fluid line tube having a first end fluidly coupled or connectable to the second compartment and a second end connectable to the fluid source, wherein the first pump port and the second pump port are placed on a first side of the casing, and the plurality of ports are placed on a second side of the casing, opposite the first side, and wherein the first compartment, the yielding pump tube, and the second compartment delimit together a fluid path extending between the at least one fluid line tube, having the first end fluidly coupled to the first compartment, and the patient line tube, to allow fluid flow at least from the at least one fluid line tube, having the first end fluidly coupled to the first compartment, through the yielding pump tube and to the patient line tube or from the patient line tube, through the yielding pump tube and to the at least one fluid line tube, having the first end fluidly coupled to the first compartment, when the peristaltic pump of the cycler is actuated.

21. The assembly of claim 20, wherein the plurality of line tubes further comprises a heater line tube having a first end fluidly coupled to the first compartment, and a heater bag fluidly coupled to a second end of the heater line tube, the heater bag being configured to be coupled to a heater of the cycler, and wherein the casing comprises a by-pass channel in fluid communication with the first compartment, the second compartment, and the heater line tube.

* * * * *